US005965524A

United States Patent [19]
Burke, Jr. et al.

[11] Patent Number: 5,965,524
[45] Date of Patent: Oct. 12, 1999

[54] ANALOGS OF VISCOSIN AND USES THEREOF

[75] Inventors: Terrance Burke, Jr., Bethesda; Bhaskar Chandrasekhar, Potomac, both of Md.; Martha Knight, Washington, D.C.

[73] Assignee: Peptide Technologies Corporation, Gaithersburg, Md.

[21] Appl. No.: 08/341,710

[22] Filed: Sep. 6, 1994

Related U.S. Application Data

[60] Continuation-in-part of application No. 07/986,059, Dec. 7, 1992, abandoned, which is a division of application No. 07/793,153, Nov. 18, 1991, Pat. No. 5,169,862, which is a division of application No. 07/376,556, Jul. 7, 1989, abandoned.

[51] Int. Cl.$^6$ .................................................. A61K 38/00
[52] U.S. Cl. .................................. 514/9; 514/11; 560/18; 530/317; 530/323; 530/328
[58] Field of Search ........................................ 530/317, 328, 530/323; 514/9, 11, 452, 453; 549/352, 355; 560/18

[56] References Cited

U.S. PATENT DOCUMENTS

| | | | |
|---|---|---|---|
| 3,997,565 | 12/1976 | Kauer | 424/278 |
| 4,020,183 | 4/1977 | Asculai et al. | 424/341 |
| 4,024,158 | 5/1977 | Kauer | 424/278 |
| 5,169,862 | 12/1992 | Burke, Jr. et al. | 514/450 |

FOREIGN PATENT DOCUMENTS

| | | |
|---|---|---|
| 44 11 025 | 10/1995 | Germany . |
| 62-263176 | 11/1987 | Japan . |

OTHER PUBLICATIONS

Berthet, "Crown Ether Derivatives" Chem Abs # 99:5986, 1983.
Detellior, Synthesis of Peptide Functional Crown Ethers Chem Abs # 100:192224, 1983.
Voggtle, "Crown Ethers of Adrenaline, Dopamine" Chem Abs # 87:5929, 1976.
Tamura, "Antibiotic" Caplus ABS # 1976:178216.
Konup, "Antimicrobial Activity of Crown–Ethers" Biosis ABS # 1989:490407.
Neu et al, Appl Microbiol Biotechol (1990) 32: 518–520.
Jacobs et al, Science vol. 260 May 7, 1993, 819–822.
Takeshima et al., "Inhibition of liver Acetyl–Co A Carboxylase" Chem. Abs. # 104:202875, 1986.
Comeau et al., "Synthesis of some Carboxystearic acids" Chem Abs. # 78:123938, 1972.
Okada et al., "Synthesis of Viscosic Acid" Chem Abs. # 77:152567, 1972.
Hitomi, H. et al., "Synthesis and Antituberculous Activity of Viscosin Analogues," Yakugaku Zasshi 88(3):299–302 (1968).
Nagai, S., et al., "Study on Surfactin, a Cyclic Depsipeptide. II. Synthesis of Surfactin B$_2$ Produced by Bacillus natto KMD 2311," Chem. Pharm. Bull. 44(1):5–10 (1996).

English Language abstract for German Patent Document No. DE 44 11 025 (Ref. AM1), Derwent WPI Accession No. 95–352039/46, (1995).
Albericio, F., and Barany, G., "Application of N,N–Dimethylformamide Dineopentyl Acetal For Efficient Anchoring of N$^\alpha$–9–Fluorenylmethyloxycarbonylamino Acids as p–Alkoxbenzyl Esters in Solid–Phase Peptide Synthesis," Int. J. Peptide Protein Res. 23:342–349 (1984).
Anwer, M.K., et al., "An Advantageous Method for the Rapid Removal of Hydrogenolysable Protecting Groups Under Ambient Conditions; Synthesis of Leucine–Enkephalin," Synthesis: 929–932 (1980).
Arnholdt, A.C., et al., "Analysis and Partial Epitope Mapping of Human T Cell Responses to Trypanosoma cruzi Cysteinyl Proteinase," J. Immunol. 151 (6):3171–3179 (Sep. 15, 1993).
Asano, M., et al., J. Pharm. Soc. Jpn. 61:220–228 (1941).
Atherton, E., et al., "Peptide Synthesis, Part 10. Use of Pentafluorophenyl Esters of Fluorenylmethoxycarbonylamino Acids in Solid Phase Peptide Synthesis," Tetrahedron 44(3):843–857 (Mar. 1988).
Balis, J., "Influence de Quelques Corps Chimiques sur la Survie in vitro de Trypanosoma evansi. III. Acides Gras," Rev. Elev. Méd. Vét. Pays Trop. 19(3):351–356 (1966).
Benz, F., et al., "Stoffwechselprodukte von Mikroorganismen. Echinocandin B, ein Neuartiges Polypeptid–Antibioticum aus Aspergillus nidulans var. echinulatus: Isolierung und Bausteine," Helv. Chim. Acta 57(8):2459–2477 (1974).
Bodanszky, M., et al., "Synthesis of Secretin. II. The Stepwise Approach," J. Am. Chem. Soc. 89(25):6753–6757 (Dec. 6, 1967).
Boné, G.J., and Parent, G., "Stearic Acid, An Essential Growth Factor for Trypanosoma cruzi," J. Gen. Microbiol. 31:261–266 (1963).
Brady, S.F., et al., "Practical Synthesis of Cyclic Peptides, With an Example of Dependence of Cyclization Yield Upon Linear Sequence," J. Org. Chem. 44(18):3101–3105 (1979).
Brener, Z., "Recent Developments in the Field of Chagas' Disease," Bulletin of the World Health Organization 60(4):463–473 (1982).
Brockmann, H., and Schmidt–Kastner, G., "Valinomycin I, XXVII. Mitteil. über Antibiotica aus Actinomyceten," Chem. Ber. 88(1):57–61 (1955).

(List continued on next page.)

Primary Examiner—Johann Richter
Assistant Examiner—Patrick R. Delaney
Attorney, Agent, or Firm—Sterne, Kessler, Goldstein & Fox P.L.L.C.

[57] ABSTRACT

This invention is directed to the analogs of viscosin, pharmaceutical compositions thereof and to methods of using viscosin and analogs thereof as biosurfactants and as antibacterial, antiviral and antitrypanosomal therapeutic compounds. In particular, compositions that inhibit the growth of the pathogens Mycobacterium tuberculosis, Herpes Simplex Virus 2 and/or Trypanosoma cruzi are disclosed.

24 Claims, No Drawings

OTHER PUBLICATIONS

Burke, T.R., Jr., et al., "Solid–Phase Synthesis of Viscosin, a Cyclic Depsipeptide with Antibacterial and Antiviral Properties," *Tetrahedron Letts.* 30(5):519–522 (Aug. 1989).

Burke, T.R., Jr., and Chandrasekhar, B., "Preparative Reversed–Phase High–Performance Liquid Chromatography in the Synthesis of Viscosin, a Cyclic Depsipeptide," *J. Chromatog.* 484:293–298 (Dec. 22, 1989).

Carpino, L.A., et al., "The 9–Fluorenylmethoxycarbonyl Function, a New Base–Sensitive Amino–Protection Group," *J. Am. Chem. Soc.* 92(19):5748–5749 (Sep. 23, 1970).

Cartwright, N.J., "The Structure of Serratamic Acid," *Biochem. J.* 67:663–669 (1957).

Chang, C.–D., et al., "Preparation and Properties of $N^\alpha$–9–Fluorenylmethyloxycarbonylamino Acids Bearing tert–Butyl Side Chain Protection," *Int. J. Peptide Protein Res.* 15:59–66 (1980).

Cunningham, L.V., et al., "Effect of Long–Chain Fatty Acids on Some Trypansomatid Flagellates," *J. Gen. Microbiol.* 70:491–496 (1972).

Daniel, T.M., "Chapter 119. Tuberculosis," in: *Harrison's Principles of Internal Medicine*, 11th Ed., Braunwald, E., et al., Eds., New York: McGraw–Hill Book Company, pp. 625–633 (1987).

DeTar, Del.F. et al., "Reactions of Carbodiimides. I. The Mechanisms of the Reactions of Acetic Acid with Dicyclohexylcarbodiimide," *J. Am. Chem. Soc.* 88(5):1013–1019 (Mar. 5, 1966).

Elliott, D.F., "Preparation of L–Threonine. Interconversion of the Four Stereoisomeric α–Amino–β–Hydroxybutyric Acids," *J. Chem. Soc.*:62–68 (1950).

Floyd, D.E., et al., "Addition of Alkylmalonic Esters to Acrylic Esters," *J. Org. Chem.* 16:882–886 (1951).

Fonken, G.S., et al., "The Synthesis of Ketones from Di–t-–butyl Malonates," *J. Am. Chem. Soc.* 74:831–833 (1952).

Fuller, W.D., et al., "Detection and Prevention of Oligopeptide Formation During the Synthesis of 9–Fluorenylmethyloxycarbonyl Amino Acid Derivatives," *Proceedings of the Eight American Peptide Symposium*, Hruby and Rich, Eds., Rockford, IL: Pierce Chemical Co., pp. 79–82 (1983).

Gäumann, E., et al., "Enniatin, ein Neues, Gegen Mykobakterien Wirksames Antibiotikum," *Experentia* 3:202–203 (1947).

Gaur, R.K., and Chauhan, V.S., "Fatty Acid Derivatives of Acidic Amino Acids as Potential Antibiotics," *Indian J. Chem.* 27B:405–408 (May 1988).

Georgiou, G., et al., "Surface–Active Compounds From Microorganisms," *Bio/Technology* 10:60–65 (Jan. 1992).

Gilon, C., et al., "A Novel Method for the Facile Synthesis of Depsipeptides," *Tetrahedron Letts.* 40:3811–3814 (1979).

Gisin, B.F., et al., "Solid–Phase Synthesis of the Cyclododecadepsipeptide Valinomcyin," *J. Am. Chem. Soc.* 91(10):2691–2695 (May 7, 1969).

Godfrey, D.G., "Influence of Dietary Cod Liver Oil Upon *Trypanosoma congolense, T. cruzi, T. vivax* and *T. brucei*," *Exptl. Parasitol.* 7:255–268 (1958).

Groupé, V., et al., "Observations on Antiviral Activity of Viscosin," *Proc. Soc. Exptl. Biol. Med.* 78:354–358 (1951).

Hamond, D.J., et al., "A Novel Series of Chemical Structures Active in vitro Against the Trypomastigote Form of *Trypanosoma cruzi*," *Trans. Royal Soc. Trop. Med. Hygiene* 78:91–95 (1984).

Haneishi, T., et al., "Antimycobacterial Activities in Vitro and In Vivo and Pharmacokinetics of Dihydromycoplanecin A," *Antimicrobial Agents and Chemotherapy* 32(1):110–116 (Jan.1988).

Hintzer, K., et al., "Access to (S)–2–Methyloxetane and the Precursor (S)–1,3–Butanediol of High Enantiomeric Purity," *J. Org. Chem.* 47:3850–3854 (1982).

Hiramoto, M., et al., "Synthesis of the Proposed Structure of Viscosin," *Biochem. Biophys. Res. Comm.* 35(5):702–706 (1969).

Hiramoto, M., et al., "The Revised Structure of Viscosin, a Peptide Antibiotic," *Tetrahedron Letts.* 13:1087–1090 (1970).

Horton, J.M., and Pankey, G.A., "Polymyxins," in: *Antimicrobial Therapy*, Ristuccia, A.M., and Cunha, B.A., Eds., New York: Raven Press, pp. 329–334 (1984).

Hubert, A.J., et al., "Le Rôle du Catalyseur dans la Cyclisation des Esters Glutamiques," *Helv. Chim. Acta* 46:1429–1445 (1963).

Jacobs, W.R., Jr., et al., "Rapid Assessment of Drug Susceptibilities of *Mycobacterium tuberculosis* by Means of Luciferase Reporter Phages," *Science* 260:819–822 (May 7, 1993).

Jaynes, J.M., et al., "In Vitro Cytocidal Effect of Novel Lytic Peptides on *Plasmodium falciparum* and *Trypanosoma cruzi*," *FASEB J.* 2(13):2878–2883 (Oct. 1988).

Kaiser E., et al., "Color Test for Detection of Free Terminal Amino Groups in the Solid–Phase Synthesis of Peptides," *Analyt. Biochem.* 34:595–598 (1970).

Khorana, H.G., "The Chemistry of Carbodiimides," *Chem. Rev.* 53:145–166 (1953).

Kisfaludy, L., et al., "Preparation and Applications of Pentafluorophenyl Esters of 9–Fluorenylmethyloxycarbonyl Amino Acids for Peptide Synthesis," *Synthesis*:325–327 (Apr. 1983).

Kochi, M., et al., "Viscosin, a New Antibiotic," *Gen. Bacteriol.*:29–30 (1951).

König, W., et al., "Eine Neue Methode zur Synthesis von Peptiden: Aktivierung der Carboxylgruppe mit Dicyclohexylcarbodiimid Unter Zusatz von 1–Hydroxybenzotriazolen," *Chem. Ber.* 103:788–798 (1970).

Laycock, M.V., et al., "Visosin, a Potent Peptidolipid Biosurfactant and Phytopathogenic Mediator Produced by a Pectolytic Strain of *Pseudomonas fluorescens*," *J. Agric. Food Chem.* 39(3):483–489 (Mar. 1991).

Levy, D., et al., "Insulin Methyl Ester. Specific Cleavage of a Peptide Chain Resulting from a Nitrogen to Oxygen Acyl Shift at a Threonine Residue," *Biochemistry* 9(16):3215–3222 (1970).

Maplestone, R.A., et al., "Retention of Native–Like Structure in an Acyclic Counterpart of a β–Sheet Antibiotic," *FEBS Letts.* 326(1–3):95–100(Jul. 12, 1993).

Matsueda, G.R., and Stewart, J.M., "A p–Methylbenzhydrylamine Resin for Improved Solid–Phase Synthesis of Peptide Amides," *Peptides* 2:45–50 (1981).

Mauger, A.B. et al., "Slow, O,N–Acyl Shift in an Actinomycin–Related Peptide Lactone," *Int. J. Peptide Protein Res.* 30:481–488 (1987).

Mercado, T.I., and Colón–Whitt, A., "Lysis of *Trypanosoma cruzi* by *Pseudomonas fluorescens*," *Antimicrobial Agents and Chemotherapy* 22(6):1051–1057 (Dec. 1982).

Mesri, E.A., et al., "Major *Trypanosoma cruzi* Antigenic Determinant in Chagas' Heart Disease Shares Homology with the Systemic Lupus Erythematosus Ribosomal P Protein Epitope," *J. Clin. Microbiol.* 28(6):1219–1224 (Jun. 1990).

Neu, T.R., et al., "Surface Active Properties of Viscosin: A Peptidolipid Antibiotic," *Appl. Microbiol. Biotechnol.* 32(5):518–520 (Feb. 1990).

Neu, T.R. and Poralla, K., "Emulsifying Agents from Bacteria Isolated During Screening for Cells with Hydrophobic Sufaces," *Appl. Microbiol. Biotechnol.* 32(5):521–525 (Feb. 1990).

Ohno, T., et al., "Constitution of Viscosin," *J. Agr. Chem. Soc. Jpn.* 27:665–669 (1953).

Okada, K., et al., "Solid Phase Synthesis of Isariin, a Long Chain β–Hydroxy Acid–Containing Cyclodepsipeptide, and its Diastereoisomer," *Chem. Pharm. Bull.* 22(9):2136–2141 (1974).

Ouaissi, M.A., et al., "*Trypanosoma cruzi* Infection Inhibited by Peptides Modeled from a Fibronectin Cell Attachment Domain," *Science* 234:603–607 (Oct. 31, 1986.).

Paine, J.B., et al., "An Improved Synthesis of Octaethylporphyrin," *J. Org. Chem.* 41 (24):3857–3860 (1976).

Paquet, A., "Introduction of 9–Fluorenylmethyloxycarbonyl, Trichloroethoxycarbonyl, and Benzyloxycarbonyl Amine Protecting Groups into O–Unprotected Hydroxyamino Acids Using Succinimidyl Carbonates," *Can. J. Chem.* 60:976–980 (1982).

Pederson, C.J., "The Discovery of Crown Ethers," *Science* 241:536–540 (Jul. 29, 1988).

Pressman, B.C., et al., "Antibiotic–Mediated Transport of Alkali Ions Across Lipid Barriers," *Proc. Natl. Acad. Sci. USA* 58:1949–1956 (1967).

Rathke, M.W., et al., "Isolation and Characterization of Lithio tert–Butyl Acetate, a Stable Ester Enolate," *J. Am. Chem. Soc.* 95(9):3050–3051 (May 2, 1973).

Rinehart, K.L., et al., "Total Synthesis of Didemnins A, B, and C," *J. Am. Chem. Soc.* 109:6846–6848 (1987).

Rosenthal, K.S., et al., "Mechanism of Action of EM 49, Membrane–Active Peptide Antibiotic," *Antimicrobial Agents and Chemotherapy* 12(6):665–672 (Dec. 1977).

Rosowsky, A., et al., "Methotrexate Analogues. 26. Inhibition of Dihydrofolate Reductase and Folylpolyglutamate Synthesis Activity and In Vitro Tumor Cell Growth by Methotrexate and Aminopterin Analogues Containing a Basic Amino Acid Side Chain," *J. Med. Chem.* 29:655–660 (1986).

Schiffler, R.J., et al., "Indigenous Chagas' Disease (American Trypanosomiasis) in California," *J. Am. Med. Assn.* 251(22):2983–2984 (Jun. 8, 1984).

Schön, I., et al., "9–Fluorenylmethyl Pentafluorophenyl Carbonate as a Useful Reagent for the Preparation of N–9–Fluorenylmethyloxycarbonylamino Acids and Their Pentafluorophenyl Esters,"*Synthesis*:303–305 (Apr. 1986).

Sheehan, J.C., et al., "Total Synthesis of a Monocyclic Peptide Lactone Antibiotic, Etamycin," *J. Am. Chem. Soc.* 95(3):875–879 (Feb. 7, 1973).

Shemyakin, M.M., et al., "The Structure–Antibmicrobial Relation of Depsipeptides," *Experientia* 19:566–568 (1963).

Shinkai, S., et al., "Temperature Regulation of Crown–Mediated Ion Transport Through Polymer/Liquid Crystal Composite Membranes. Remarkable Transport Ability of Fluorocarbon–Containing Crown Ethers," *J. Am. Chem. Soc.* 109:4458–4464 (1987).

Shute, R.E., et al., "Analogue of the Crytostatic and Antimitogenic Agents Chlamydocin and HC–Toxin: Synthesis and Biological Activity of Chloromethyl Ketone and Diazomethyl Ketone Functionalized Cyclic Tetrapeptides," *J. Med. Chem.* 30:71–78 (1987).

Storm, D.R., et al., "Polymyxin and Related Peptide Antibiotics," *Ann. Rev. Biochem.* 46:723–763 (1977).

Timm, S.L., et al., "Fatty Acids of *Trypanosoma cruzi*," *Compar. Biochem. Physiol.* 71B(3):397–402 (1982).

Tosteson, D.C., et al., "The Effect of Valinomycin on Potassium and Sodium Permeability of HK and LK Sheep Red Cells," *J. Gen. Physiol.* 50:2513–2525 (1967).

Tosteson, D.C., "Effect of Macrocyclic Compounds on the Ionic Permeability of Artificial and Natural Membrances," *Fed. Proc.* 27(6):1269–1277 (Nov.–Dec. 1968).

Ungaro, R., et al., "Substituent Effects on the Stability of Cation Complexes of 4'–Substituted Monobenzo Crown Ethers," *J. Am. Chem. Soc.* 98(17):5198–5202 (Aug. 18, 1976).

Vining, L.C., and Taber, W.A., "Isariin, a New Depsipeptide from *Isaria cretacea*," *Can. J. Chem.* 40:1579–1584 (1962).

Vogler, K., et al., "Fettsäurehaltige Basische Peptide mit Antibakterieller Wirkung," *Helv. Chim. Acta* 47:526–544 (1964).

Wang, S.–S., "p–Alkoxybenzyl Alcohol Resin and p–Alkoxybenzyloxycarbonylhydrazide Resin for Solid Phase Synthesis of Protected Peptide Fragments," *J. Am. Chem. Soc.* 95(4):1328–1333 (Feb. 21, 1973).

Wang, S.–S., "Solid–Phase Synthesis of Protected Peptide Hydrazides. Preparation and Application of Hydroxymethyl Resin and 3–(p–Benzyloxphenyl)–1, 1–DimethylpropyloxYcarbonylhydrazide Resin," *J. Org. Chem.* 40(9):1235–1239 (1975).

White, B.D., et al., "Peptide Side–Arm Derivatives of Lariat Ethers and Bibrachial Lariat Ethers: Syntheses, Cation Binding Properties, and Solid State Structural Data," *J. Org. Chem.* 54:937–947 (Feb. 1989).

Worley, D.E., and Thompson, P.E., "Experimental Studies on *Obeliscoides cuniculi*, a Trichostrongylid Stomach Worm of Rabbits. II. Antihelminthic Studies in the Dutch Rabbit," *J. Parasitol.* 49(1):51–54 (Feb. 1963).

Yagi, K., et al., "Antifungal Activity of Crown Ethers," *J. Incl. Phenomena* 2:179–184 (1984).

English Abstract for Japanese Patent Publication No. JP 62–263176 (Doc. Ref. No. AL1), Derwent WPI Acc. No. 87–359768/51, (1987).

Gaur, R.K., and Chauhan, V.S., "Fatty Acid Derivatives of Acidic of Amino Acids as Potential Antibiotics," *Indian J. Chem.* 27B:405–408 (May 1988).

ANALOGS OF VISCOSIN AND USES THEREOF

RELATED APPLICATIONS

This application is a Continuation-In-Part of U.S. Ser. No. 07/986,059, filed Dec. 7, 1992, now abandoned, which is a Divisional of U.S. Ser. No. 07/793,153, filed Nov. 18, 1991, which issued as U.S. Pat. No. 5,169,862 on Dec. 8, 1992 and which is a Divisional of U.S. Ser. No. 07/376,556, filed Jul. 7, 1989, now abandoned.

FIELD OF THE INVENTION

This invention is in the field of pharmaceutical compounds, specifically directed to analogs of viscosin and to their uses as biosurfactants and as antibacterial, antiviral and antitrypanosomal therapeutic compounds.

BACKGROUND OF THE INVENTION

Chagas' Disease

Trypanosomal diseases include some of the most pervasive and problematic illnesses facing man today. Of these, Chagas' disease (American trypanosomiasis), which is concentrated principally in Central and South America, is of particular concern, both for the number of individuals infected and for the lack of adequate chemotherapy to treat the disease (Brener, Z., *Bull. WHO* 60:463–473 (1982); Hammond et al., *Trans. Royal Soc'y Trop. Med. Hyg.* 78:91–95 (1984)). In adults, the chronic form of Chagas' disease results in cardiomyopathy, megaesophagus, megacolon and death. (Webster, L., Chapter 43 in *Goodman and Gilman's the Pharmaceutical Basis of Therapeutics,* Gilman, A., et al., eds., 8th Ed., p. 1008, Pergamon Press, New York (1990)).

Although estimates of the extent of Chagas' disease vary, it is generally agreed that from 10 to 20 million people are presently infected, representing in some reporting areas up to 43% of the total population. (Kolberg, R., *Science* 264:1859–1861 (1994)). While the causative agent for Chagas' disease, *Trypanosoma cruzi*, is transmitted predominantly in rural areas by the reduviid bug, the disease is finding its way into urban areas through blood transfusion (Brener, A., *Pharmacol. Ther.* 7:71–90 (1979)). Chagas' disease is not presently considered to be a significant problem in North America, with only a few cases of indigenous Chagas' disease having been reported in the United States. (See, e.g., Schiffler, R. J., et al., *JAMA* 251:2983–2984 (1984)). However, *T. cruzi* is found in mammals and insects across the southern United States, as far north as Virginia (Downs, W. G., *J. Parasit.* 49:50 (1963)).

Although two agents which abolish parasitemia in the acute phase are presently available (Nifurtimox (3-methyl-4-(5-nitrofurfurylidineamino) tetrahydro-4H-1,4-thiazine-1, 1-dioxide)and Benznidazole(N-benzyl-2-nitro-1-imidazoleacetamide); Keierszenbaum, F., in *Trop. Med. Parasit.*, Mansfield, ed., Marcel Dekker, New York (1984)), neither results in a complete cure and both have serious side effects. Because of toxicity and the inability to completely abolish parasitemia with certainty, these drugs are recommended as treatments for individuals with chronic Chagas' disease only because of the seriousness of the disease and the lack of superior drugs. (Webster, L., Chapter 43 in *Goodman and Gilman's the Pharmaceutical Basis of Therapeutics,* Gilman, A., et al., eds., 8th Ed., p. 1011, Pergamon Press, New York (1990)). The unavailability of adequate chemotherapeutic agents for the treatment of chronic Chagas' disease underlies the need for new antichagasic drugs.

Tuberculosis

Tuberculosis (TB, consumption of phthisis) is a contagious disease that has resulted in millions of human deaths over the centuries. Robert Koch identified the causative agent of TB, *Mycobacterium tuberculosis* (M. tb. or tubercle bacilli), in 1882. (U.S. Congress, Office of Technology Assessment, *The Continuing Challenge of Tuberculosis*, OTA-H-574, U.S. Government Printing Office, Wash., D.C., (1993), pp. 1–2. *M. bovis,* a species closely related to M. tb., also causes TB in humans (Wolinsky, E., Chapter 37 in *Microbiology: Including Immunology and Molecular Genetics,* 3rd Ed., Davis et al., eds., Harper & Row, Philadelphia (1980), pp. 723–742). Despite a century of research, TB remains the largest cause of death in the world from a single infectious disease and accounts for as much as 40% of deaths in individuals coinfected with Human Immunodeficiency Virus (HIV) in some developing countries. (Jacobs, W. R., et al., *Science* 260:819–822 (1993)). Although antibiotic therapy for TB has been successfully applied for some years, multidrug-resistant tuberculosis (MDR-TB) strains have arisen recently in several countries. Cases of MDR-TB are more difficult to treat than antibiotic-sensitive TB, and can be fatal even when the best available treatment is applied. (U.S. Congress, Office of Technology Assessment, *The Continuing Challenge of Tuberculosis*, OTA-H-574 U.S. Government Printing Office, Wash., D.C. (1993), p. 6.) Mortalities from MDR-TB strains range from 40 to 60% in immunocompetent individuals and >80% in immunocompromised individuals. (Bloom, B. R., et al., *Science* 257:1055–1064 (1992); Jacobs, W. R., et al., *Science* 260:819–822 (1993).)

As a result of these and other factors, the U.S. Office of Technology Assessment has concluded that there is a heightened need for new anti-TB drugs. (U.S. Congress, Office of Technology Assessment, *The Continuing Challenge of Tuberculosis,* OTA-H-574, U.S. Government Printing Office, Wash., D.C. (1993), p. 78.) In much the same way that it responded to public demands for increased access to anti-AIDS drugs, the U.S. Food and Drug Administration (FDA) has developed programs for the accelerated approval of anti-TB drugs that include such features as accepting surrogate endpoints (interim outcomes) and foreign clinical data in its reviews of such drugs. (Id.). Thus, the Federal government has officially recognized the need for new anti-TB drugs.

Biosurfactants

Surfactants are amphiphilic compounds that comprise both hydrophilic and hydrophobic domains within the same molecule and thus partition preferentially at interfaces between fluid phases of different degrees of polarity and hydrogen bonding (e.g., oil/water and air/water interfaces). Industrial applications for surfactants include emulsification, foaming, detergency, wetting and phase dispersion or solubilization. (Georgiou, G., et al. *Bio/Technology* 10:60–65 (1992).)

Biosurfactants are biologically produced molecules, such as peptides, which function as surfactants. Many biosurfactants are comparable to synthetic surfactants in terms of their ability to act as emulsifiers and their chemical stability. However, unlike most synthetic surfactants, biosurfactants are easily biodegradable and are thus especially suited for environmental purposes such as bioremediation and the emulsification and dispersion of oil spills. (Georgiou, G., et al. *Bio/Technology* 10:60–65 (1992); *Trends in Biotech.* 11 (1993).) Biosurfactants are also used as chemical reagents for, e.g., effecting emulsification or cell lysis. For example, a lipopeptidic biosurfactant from *Bacillus subtilis* known as Surfactin is commercially available for these and other uses. (Sigma Chemical Co. Catalog, p. 944 (1991)).

SUMMARY OF THE INVENTION

In an effort to develop new compounds for the treatment of Chagas' disease, viral disease and TB, and for use as biosurfactants, the inventors analyzed the metabolic products of the Pseudomonas species. An antitrypanosomal factor had previously been discovered from *P. fluorescens* (Mecado et al., *Antimicrobial Agents and Chemotherapy* 22:1051–1057 (1982)), which proved to be lytic on *T. cruzi*. The inventors studied the peptide lactone viscosin, which had been shown to have antiviral and antimicrobial activity against various mycobacteria. Preliminary in vitro testing against *T. cruzi* produced trypanosomal lysis in the absence of significant hemolysis. This result was subsequently supported by promising in vivo activity in mice. To pursue these initial indications, viscosin and a number of analogs were prepared by solid-phase peptide synthesis in an effort to define structural characteristics favorable to antitrypanosomal activity. The invention is directed to analogs of viscosin, pharmaceutical compositions thereof and to their use as antibacterial, antiviral and antitrypanosomal therapeutic compounds and biosurfactants.

DETAILED DESCRIPTION OF THE INVENTION

Viscosin, is a peptide lactone composed of alternating D and L amino acids with a β-D-hydroxydecanoyl dipeptide side chain. Viscosin has antibacterial, antiviral, antitrypanosomal and biosurfactant activities. (Kochi, M., et al., *Bact. Proc.* 29–30 (1951); Groupe, V., et al., *Proc. Soc'y Exptl. Biol. Med.* 78:354–358 (1951); Mercado, T., et al., *Antimicrobial Agents and Chemotherapy* 22:1051–1057 (1982); Neu, T., et al., *Appl. Microbiol. Biotechnol.* 32:518–520 (1990) and Laycock, M., et al., *J. Agric. Food Chem.* 39:483–489 (1991)). The synthesis of viscosin by solid phase methods utilizing an acid sensitive resin and a combination of Fmoc/Boc amino protection is described in Example 1.

In an effort to develop biosurfactants and antichagasic antiviral and/or antituberculous agents based on viscosin, a series of analogs were prepared which were synthetically more accessible. One aspect of this invention involves alteration of the peptide side chain and ring junction. Side chain analogs consist of a variety of linear fatty acyl or aliphatic amides while modifications in the ring junction involve replacing the D-allo-Thr with D-Thr. Synthesis of these analogs is based on those techniques used to prepare viscosin itself, and rely on the novel use of activated esters of pentafluorophenol for the coupling of unprotected hydroxyl-bearing amino acids.

A second aspect of this invention addresses the rate of ion transport in viscosin's antitrypanosomal activity and involves replacement of the peptide lactone ring with a crown ether. In general, any crown ether that has ionophore properties may be substituted for the peptide lactone ring of viscosin. Preferable crown ethers include benzo-15-crown-5 polyether, dibenzo-18-crown-6 polyether, dibenzo-24-crown-8 polyether, 2-hydroxymethyl-12-crown-4, 2-hydroxymethyl-15-crown-5 polyether, and 2-hydroxymethyl-18-crown-6 polyether. A most preferable crown ether is benzo-15-crown-5 polyether. These analogs may further differ from each other in the side chain (R group) which may be long chain alkylamides or simple peptides.

The viscosin analogs comprising crown ethers may be prepared according to the general methods of synthesis set forth in the Example 1 of the application. For example, where the crown ether is fused to a benzene ring, it is possible to nitrate the ring with nitric acid, followed by reduction to give the amine followed by the condensation thereof with an appropriate side chain precursor to give the viscosin derivative.

Visconsin is a cyclic depsipeptide with the following formula:

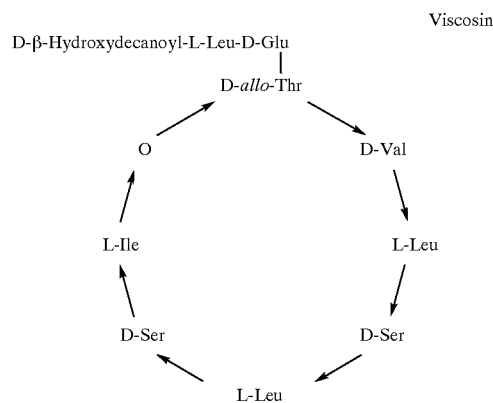

Unless indicated otherwise, abbreviations for amino acids used herein are as given in 37 C.F.R. §1.822 (Jul. 1, 1993).

Cyclic peptide analogs of this invention may have the following Formula I:

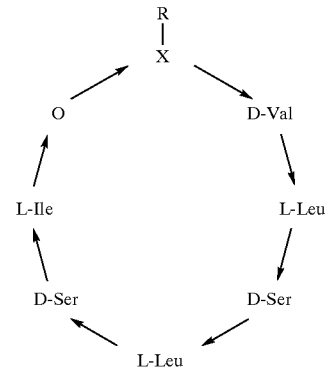

wherein X is D-allo-Thr, D-Thr, D-Ser, or Homoserine (HomoSer) and wherein R is D-3-hydroxydecanoyl-L-Leu-D-Glu, Decanoyl-L-Leu-D-Glu, Octadecanoyl, a $C_2$ to $C_{22}$ linear fatty acyl amide, an aliphatic amide, D-3-hydroxydecanoyl-L-$X_1$-$X_2$, wherein $X_1$ is Ile, Val, Gly, or Norisoleucine (NorIle) and wherein $X_2$ is D-Asp, D-γGlu, D-βAsp, Succinic acid, or dicarboxylic acid, provided that X is not D-allo-Thr when R is D-3-hydroxydecanoyl-L-Leu-D-Glu.

The cyclic peptide analogs of the invention may also be derivatives of Formula I in which D-allo-Thr is replaced by 2,4-diaminobutyric acid (Dbu), and in which the ester linkage in viscosin is replaced by an amide bond between Dbu and L-Ile, and having the following Formula IA:

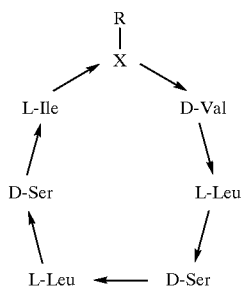

wherein X is Dbu, and wherein R is D-3-hydroxydecanoyl-L-Leu-D-Glu, Decanoyl-L-Leu-D-Glu, Octadecanoyl, a $C_2$ to $C_{22}$ linear fatty acyl amide, an aliphatic amide, D-3-hydroxydecanoyl-L-$X_1$-$X_2$, wherein $X_1$ is Ile, Val, Gly, or NorIle and wherein $X_2$ is D-Asp, D-γGlu, D-βAsp, Succinic acid, or dicarboxylic acid. Substitution of D-allo-Thr with Dbu maintains the remaining amino acids of the ring and the total number of ring atoms relative to viscosin.

In a related embodiment, the cyclic peptides of the invention may be derivatives of Formula I in which the ester linkage in viscosin is replaced by an amide bond, and in which the L-Ile residue in viscosin is deleted and Lys or Ornithine (Orn) is substituted for D-allo-Thr, having the following Formula IB:

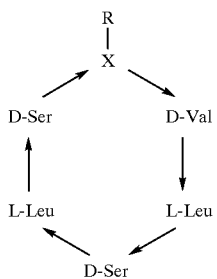

wherein X is D- or L- Lys or Orn, and wherein R is D-3-hydroxydecanoyl-L-Leu-D-Glu, Decanoyl-L-Leu-D-Glu, Octadecanoyl, a $C_2$ to $C_{22}$ linear fatty acyl amide, an aliphatic amide, D-3-hydroxydecanoyl-L-$X_1$-$X_2$, wherein $X_1$ is Ile, Val, Gly, or NorIle and wherein $X_2$ is D-Asp, D-γGlu, D-βAsp, Succinic acid, or dicarboxylic acid. Replacement of D-allo-Thr with Lys with the concomitant removal of L-Ile maintains the ring size relative to that of viscosin. In contrast, substitution of Orn for D-allo-Thr and Ile results in a ring structure that is contracted by one carbon atom and thus may adopt a different conformation than the Lys-containing analogs.

Linear analogs of this invention may have the following Formula II:

D-3-hydroxydecanoyl-L-Leu-D-Glu-X-D-Val-L-Leu-D-Ser-L-Leu-D-Ser-L-Ile-OH wherein X is D-allo-Thr, D-Thr; or D-3-Hydroxydecanoyl-L-Leu-D-Glu-HN$_2$; or

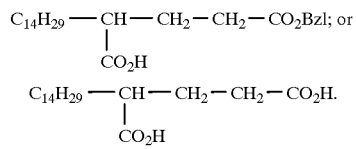

Peptidomimetics or "crown ether" analogues of this invention have the following Formula III:

Formula III

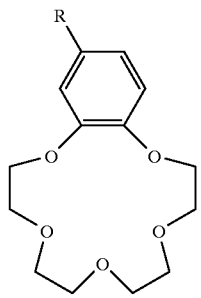

wherein R is D-3-Hydroxydecanoyl-L-Leu-OBzl-D-Glu-NH;

D-3-Hydroxydecanoyl-L-Leu-D-Glu-NH;

Decanoyl-L-Leu-OBzl-D-Glu-NH;

Decanoyl-L-Leu-D-Glu-NH;

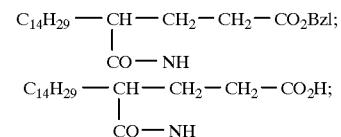

CH$_3$CONH (AcNH);

linear $C_2$–$C_{22}$ amides; or

D-3-hydroxydecanoyl-L-$X_1$-D-$X_2$-NH or Decanoyl-L-$X_1$-D-$X_2$-NH, wherein $X_1$ is a neutral amino acid and wherein $X_2$ is an acidic or a neutral amino acid.

As is known in the art, amino acid substitutions may be made to modulate finely the characteristics of the analogs, provided the analog still has biological activity. Thus, original residue Leu may be substituted with Ile or Val; original residue Val may be substituted with Ile or Leu; original residue Ser may be substituted with Thr; original residue Ile may be substituted with Leu or Val; and original residue Thr may be substituted with Ser.

The peptide analogs of the invention have antichagasic activity. Thus, these analogs are useful as therapeutic compounds for typanosomal mediated diseases, such as Chagas' disease. Additionally or alternatively, Viscosin analogs have antimycobacterial activity, and are thus useful for the treatment of TB, and/or antiviral activities. Of particular interest is the use of these analogs as a topical therapeutic in treating skin lesions, such as those caused by Herpes Simplex and Herpes Complex viruses. Furthermore, viscosin analogs function as biosurfactants and are useful as emulsifying agents, particularly when it is desired to use biodegradable surfactants or surfactants which are compatible with biological molecules.

The dose ranges for the administration of the viscosin analogs of the invention are those which are large enough to produce the desired effect whereby the symptoms of bacterial, viral or trypanosomal infection are ameliorated. Generally, the dosage will vary and will be adjusted by the patient's physician according to factors such as the age, sex and immunological status of the patient, the extent of disease in the patient, and contraindications, if any. Dosages can vary from 0.01 mg/kg to 10 mg/kg, preferably 0.01 mg/kg to 0.1 mg/kg, of the viscosin analogs of the invention in one or more administrations daily, for one or several days. The viscosin analogs of the invention can be administered parenterally by injection or by gradual perfusion over time. They can also be administered intravenously, intraperitoneally, intramuscularly, subcutaneously or by inhalation.

Preparations for parenteral administration include sterile or aqueous or non-aqueous solutions, suspension, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobial agents, anti-oxidants, chelating agents, inert gases and the like. (See, generally, *Remington's Pharmaceutical Science*, 16th Ed., Osol, A., ed., Mack, Easton, (1980)).

The invention also relates to a method for preparing a medicament or pharmaceutical composition comprising the components of the invention, the medicament being used for therapy of bacterial, viral, and trypanosomal infection in animals.

An exemplary list of causative agents for diseases and conditions that may be treated by the analogs of this invention includes microbes and protozoa, such as *Bacteroides fragilis*, Fusobacterium spp, *Bordetella pertussis*, *Haemophilus influenzae*, *Yersinia enterocolitica*, *Yersinia pestis*, *Branhamella catarrhalis*, *Escherichia coli*, *Klebsiella pneumonia*, *Vibrio cholerae*, *Proteus mirabilis*, *Pseudomonas aeruginosa*, *Serratia marcescens*, *Neisseria meningitidis*, *Salmonella typhimurium*, *Salmonella typhi*, *Salmonella paratyphi B*, *Mycobacterium leprae*, *Chlamydia trachomatis*, Shigella spp., *Staphylococcus aureus*, *Pseudomonas aeruginosa*, Clostridium spp., *Escherichia coli*, *Yersinia pestis*, *Vibrio cholerae*, *Bordetella pertussis*, *Streptococcus pyogenes bacterium*, *Streptococcus mutans*, Plasmodium spp., Toxoplasma spp., Leishmania spp., Schistosoma spp., Trypanosoma spp., *Mycoplasma pneumoniae*, *Mycoplasma hominis*, and Streptococcus spp. In one embodiment of the invention, the analogs and methods of the invention are used to treat diseases caused by Mycobacterial species, particularly those caused by *Mycobacterium tuberculosis, M. intracellulare, M. bovis, M. gordonae, M. kansasii*, and *M. nonchromogenicum*.

Viral agents that may be treated by the compositions and methods of the inventions include retroviruses (HTLV-I, HTLV-II, HIV-1, HIV-2, feline leukemia virus), myxoviruses (influenza A H1-H12, influenza B, influenza C), paramyxoviruses (parainfluenze 1–4, Newcastle disease virus, measles virus, respiratory syncytial virus, parotitis virus, distemper virus), hepatitis A virus, human rhinoviruses 1–113, rota viruses, herpes viruses (HSV-1, HSV-2, cytomegalovirus, Epstein-Barr virus, equine abortion virus), papova viruses (BK virus, human wart virus), parvo viruses (mink enteritis virus, bovine parvo virus, feline parvo virus, procine parvo virus), human hepatitis B virus, Ebola and Marburg viruses, and adenoviruses (human adenoviruses 1–33).

In the examples that follow, numbers have been assigned to fragments, compounds and analogs for ease in referring to them in the text. These fragments, compounds, and analogs are as follows:

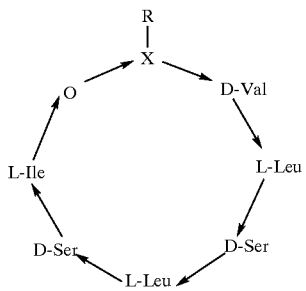

1: X = D-allo-Thr;   R = D-3-Hydroxydecanoyl-L-Leu-D-Glu
2: X = D-Thr;        R = D-3-Hydroxydecanoyl-L-Leu-D-Glu
3: X = D-allo-Thr;   R = Decanoyl-L-Leu-D-Glu
4: X = D-allo-Thr;   R = Octadecanoyl D-3-Hydroxydecanoyl-L-Leu-D-Glu-X-D-Val-L-Leu-D-Ser-L-Leu-D-Ser-L-Ile-OH 5: X = D-allo-Thr
6: X = D-Thr
7: D-3-Hydroxydecanoyl-L-Leu-D-Glu-NH$_2$ 8: 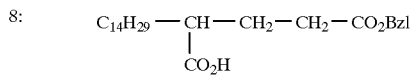

-continued

9: 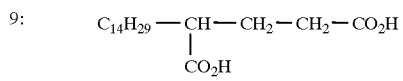

10: R = D-3-Hydroxydecanoyl-L-Leu-O-Bzl-D-Glu-NH
11: R = D-3-Hydroxydecanoyl-L-Leu-D-Glu-NH
12: R = Decanoyl-L-Leu-OBzl-D-Glu-NH
13: R = Decanoyl-L-Leu-D-Glu-NH

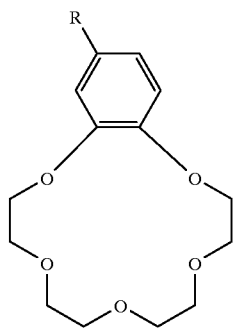

14: R = 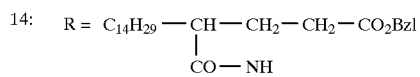

15: R = 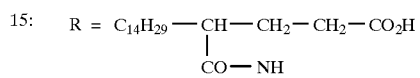

16: R = AcNH
17: D-Hydroxydecanoyl-L-Leu-Gly-L-Ser-D-Val-L-Thr-L-Leu-OH
18:
    D-3-Hydroxydecanoyl-L-Leu-(OBzl)-D-Glu-D-allo-Thr-D-Val-L-Leu-(OBzl)
    D-Ser-L-Leu-(OBzl)-D-Ser-OH               |
                                    H-Ile-O

19:

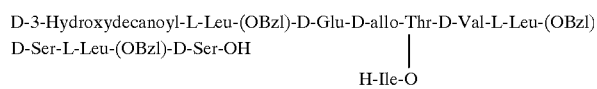
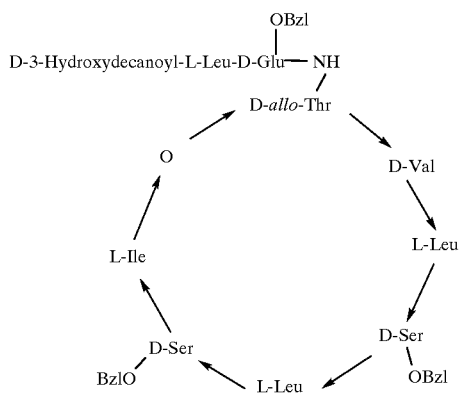

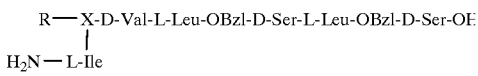

20: X = D-Thr;            R = 3-D-Hydroxydecanoyl-L-Leu-D-Glu
21: X = D-allo-Thr;      R = Decanoyl-L-Leu-D-Glu
22: X = D-allo-Thr;      R = Octadecanoyl
23: (±)-3-hydroxydecanoic acid
24: pentafluorophenyl (Pfp) D-3-hydroxydecanoate
25: D-allo-Thr
26: Fmoc-D-allo-Thr
27: Fmoc-D-allo-Thr-Pfp
28: alkoxybenzyl alcohol resin
29: Fmoc-D-Thr-Pfp -continued
30: R = NO$_2$
31: R = NH$_2$
32: R = Boc-OBzl-D-Glu-NH
33: R = Boc-L-Leu-OBzl-D-Glu-NH
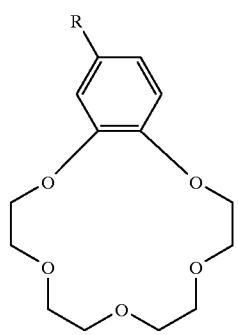
34:
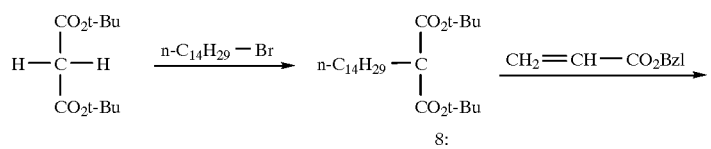
8:
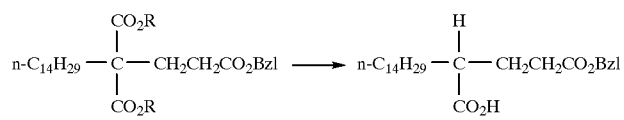
35: R = t-Butyl
36: R = H
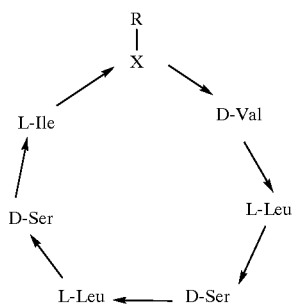
37: X = 2,4-diaminobutyric acid (Dbu)
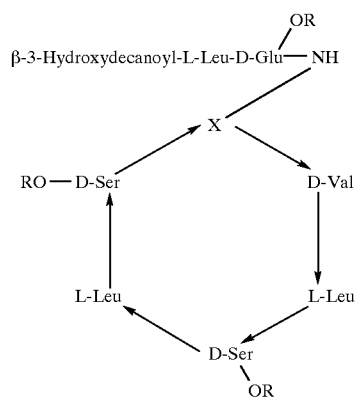
38: X = D-Lys, R = Bzl
39: X = D-Lys, R = H
40: X = D-Orn, R = Bzl
41: X = D-Orn, R = H

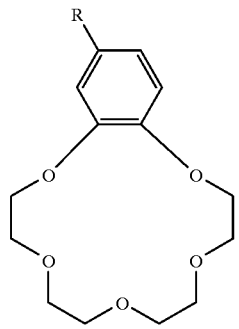

42: R = Octadecanoyl

EXAMPLE 1

Solid-phase Synthesis of the Cyclic Depsipeptide Viscosin

During the screening of microorganisms for antibiotic substances by Kochi at the Yokohama Medical College, a substance was isolated from a culture of *Pseudomonas viscosa* and was eventually shown to have antiviral activity (Groupe, V., et al., *Proc. Soc. Exptl. Biol. Med.* 78:354–358 (1951)), antimicrobial activity against various mycobacteria (Kochi, M., et al., *Bact. Proc.* 29–30 (1951)), and activity as a surfactant that facilitates pseudomonal infection of broccoli (Neu, T. R., et al., *Appl. Microbiol. Biotechnol.* 32:518–520 (1990); Laycock, M. V., et al., *J. Agric. Food Chem.* 39:483–489 (1991)). The purified active substance was given the name viscosin. Structure (17) was proposed from the initial examination of viscosin which showed it to be a monocarboxylic peptide containing the fatty acid (−)-D-3-hydroxydecanoic acid (Ohno, T., et al., *J. Agr. Chem. Soc. Japan.* 27:665–669 (1953)).

Studies of synthetic peptides based on or derived from the incorrect structure failed to yield compounds having antimycobacterial activity equivalent to that of biologically-produced viscosin (Hitomi, H., et al., Yakugaku Zasshi 88:299–302 (1968)). Confirmation that the proposed linear structure was incorrect was shown by comparison of natural material with the synthetic structure (1) obtained by solution synthesis (Hiramoto, M., et al., *Biochem. Biophys. Res. Commun.* 35:702–706 (1969)). The revised structure (1) was proposed based on further physical characterization which indicated viscosin to be a cyclic depsipeptide (a peptide lactone) having alternating D- and L-amino acids with an amino-terminal D-3-hydroxydecanoyl group (Hiramoto, M., et al., *Tetrahedron Lett.* 13:1087–1090 (1970)). Ring closure is through an ester linkage between the carboxyl of L-Ile and the hydroxyl of D-allo-Thr, leaving the gamma-carboxyl of D-Glu free. To further strengthen the structural assignment, work was undertaken to prepare structure (1) by a scheme which utilized solid-phase techniques.

Viscosin was prepared by solid-phase chemistry using an Fmoc-protocol starting with an alkoxybenzyl alcohol resin. Cyclization with the activating agent bis (2-oxo-3-oxazolindyl) phosphinic chloride (BOP-Cl) gave a product which was indistinguishable from natural viscosin, thereby supporting the structure proposed therefor (Burke, T. R., et al., *Tetrahedron Ltrs.* 30:519–522 (1989)).

A potentially challenging aspect of the synthesis of cyclic despipeptides is ring closure. It has been found that ring closure is most advantageously effected through amide bond formation rather than through ester formation, and there are numerous examples of such cyclizations (Rinehart, K. L., et al., *J. Amer. Chem. Soc.* 109:6846–6848 (1987); Okada, K., et al., *Chem. Pharm Bull.* 22:2136–2141 (1974); Gilon, C., et al., *Tetrahedon Ltrs.* 40:3811–3814 (1979); Shute, R., et al., *J. Med. Chem.* 30:71–78 (1987); Sheenan, J., et al., *J. Amer. Chem. Soc'y* 95:875–879 (1973); Gisin, B., et al., *J. Amer. Chem. Soc'y* 91:2691–2695 (1969)). One problem with the use of solid-phase synthesis in the preparation of cyclic depsipeptides has been the difficulty of maintaining full side-chain protection in the linear precursor during resin cleavage by HF. In an effort to use recent techniques of solid-phase synthesis for the preparation of cyclic depsipeptides, a scheme was developed to employ these techniques in the synthesis of viscosin. Examination of viscosin shows that linear precursor having structure (18) (see below) would be a suitable target for preparation by solid-phase synthesis as cyclization yielding the desired benzyl-protected viscosin (19) would result from amide bond formation between the C-terminal carboxyl of OBzl-D-Ser and the amino group of L-Ile. To prepare structure (18) by solid-phase synthesis and preserve the benzyl protecting groups during cleavage from the resin, a synthetic scheme was employed using fluorenylmethoxycarbonyl (Fmoc) protected amino acids (Carpino, L. A., et al., *J. Amer. Chem. Soc.* 92:5748–5749 (1970)) and the acid-sensitive alkoxybenzyl alcohol resin of Wang (Wang, S. S., *J. Amer. Chem. Soc.* 95:1328–1333 (1973)), which can be cleaved with 50% trifluoroacetic acid (TFA) in $CH_2Cl_2$. The choice of butyloxycarbonyl-amino protection for Ile relies on its stability to the conditions of Fmoc deprotection during peptide synthesis. However, treatment of the resin with TFA would simultaneously remove the butyloxycarbonyl (Boc) group and cleave the peptide from the resin, yielding structure (18) directly with both amino and carboxy termini deprotected for cyclization. The value of simultaneous deprotection of amino and carboxyl terminal groups leading directly to material suitable for cyclization has been shown in solution synthesis (Shute, R. E., et al., *Tetrahedron Lett.* 28:3419–3422 (1987)).

Coupling of amino acids through D-Val followed a standard Fmoc-based protocol. In summary, Fmoc-OBzl-D-Ser (all Fmoc-amino acids were either purchased or synthesized as crystalline solids using Fmoc-N-hydroxysuccinimide ester (Paguet, A., *Can. J. Chem.* 60:976–980 (1982))) was coupled to alkoxybenzyl alcohol resin (1.0 mmol —OH $g^{-1}$ resin) using dicyclohexylcarbodiimide (DCC) activation in the presence of 0.1 eq. of dimethylaminopyridine (DMAP)

(Wang, S. S., *J. Org. Chem.* 40:1235–1239 (1975)), to yield 0.4 to 0.6 mmol/g resin. After capping the resin with benzoyl chloride (Wang, S. S., *J. Amer. Chem. Soc.* 95:1328–1333 (1973)), the synthesis was continued through Fmoc-D-Val using the following protocol for sequential coupling of Fmoc-amino acids to the growing peptide chain: 1) three N,N'-dimethylformamide (DMF) washes, 2) three $CH_2Cl_2$ washes, 3) amine deprotection using piperidine:DMF, 1:1 v/v, 20 min, 4) coupling amino acid using 2.5 eq of Fmoc amino acid, hydroxybenzotriazole (HOBT) (Konig, W. et al., *Chem. Ber.* 103:788–798 (1970)) and DCC in DMF, 2–3 hr, 5) monitoring of coupling using the Kaiser ninhydrin test (Kaiser, R. L. et al., *Anal. Biochem.* 34:595–598 (1970)), and 6) repeating the coupling if not completed. Single couplings were adequate for Fmoc-OBzl-D-Ser and Fmoc-D-Val, with multiple couplings being required for Fmoc-L-Leu approximately 50% of the time.

An important aspect of the use of solid-phase chemistry in the synthesis of cyclic depsipeptides is the preparation of the ester branch point while the peptide is still attached to the resin. In this regard, the strategy for building the Boc-L-Ile ester branch point called for the addition of Fmoc-D-allo-Thr with its side chain hydroxyl unprotected. Although such coupling of an unprotected Thr is known in solution synthesis, it has been assumed that this was incompatible with solid-phase synthesis due to self-acylation resulting from the large excess of amino acid needed to achieve high coupling efficiency. Since direct DCC mediated coupling could result in significant acylation of the unprotected hydroxyl (Stewart, J. M. et al., 153rd Annual Meeting of the American Chemical Society, April 1967), coupling was achieved using the pentafluorophenyl ester (Pfp) (Kisfaludy, L. et al., *Synthesis* 325–327 (1983)), which reacts rapidly with amines, but sluggishly with alcohols. Although D-allo-Thr is not readily commercially available, epimerization of D-Thr gave an inexpensive source of D-allo-Thr (Elliot, D. F., *J. Chem. Soc.* 62–68 (1950)). This was first protected as the Fmoc derivative, then esterified with pentafluorophenol/DCC to yield Fmoc-D-allo-Thr-Pfp before coupling cleanly and quantitatively to the resin in a single coupling reaction using 2.5 eq. of amino acid, 5 hr in DMF. As anticipated, examination of a sample of TFA-cleaved resin by HPLC gave no indication of significant acylation of the D-allo-Thr hydroxyl.

It was anticipated that esterification of the Fmoc-D-allo-Thr hydroxyl with Boc-L-Ile directly could lead to side-product formation due to O→N shift of Boc-Ile under the conditions which would subsequently be necessary to deblock the Fmoc-D-allo-Thr (Levy, D., et al., *Biochemistry* 9:3215–3222 (1970); Mauger, A. B., et al., *Int. J. Peptide Protein Res.* 30:481–488 (1987)). Since the reverse, N→O shift would not be expected to occur under the non-acidic conditions of the synthesis, the resin was first deblocked with piperidine in the usual manner and then coupled with Fmoc-OBzl-D-Glu-Pfp. Again, the use of Pfp activation allowed amino coupling to occur without acylation of the unprotected hydroxyl. The free hydroxyl of D-allo-Thr was then esterified with Boc-L-Ile/DCC activation (with 0.1 eq. of DMAP (Gilon, C., et al., *Tetrahedron Lett.* 40:3811–3814 (1979))) to give the desired Fmoc-OBzl-D-Glu-(O-Boc-L-Ile)-D-allo-Thr branch point as a single major product on HPLC.

Having successfully prepared the branch point, it was then found that piperidine deblocking of Fmoc-OBzl-D-Glu followed by coupling with Fmoc-L-Leu (DCC/HOBT) gave a major side product which was at times equal to 40% of the desired product. This chain-terminated side product gave amino acid analysis and fast atom bombardment (FAB) mass spectral data consistent with the cyclization (Hubert, A. J. et al., *Helv. Chim. Acta* 46:1429–1445 (1963)) of the OBzl-D-Glu to pyroglutamic acid. This was readily removed chromatographically and in subsequent synthesis was essentially eliminated by decreasing the piperidine deblock time to 5 min.

A linear peptide having structure (18) was completed by acylating the peptide resin with the Pfp-ester of D-3-hydroxydecanoic acid in DMF. Again, the use of Pfp ester activation allowed the acid to be coupled with its hydroxyl unprotected. 3-Hydroxydecanoic acid (mp 55°–56° C., 57° C.) (Cartwright, N. J., *Biochem. J.* 67:663–669 (1957)) was synthesized from n-octyl aldehyde by reaction with lithium tert-butyl (t-Bu) acetate (Rathke, M. W., et al., *J. Amer. Chem. Soc.* 95:3050–3051 (1973)) followed by TFA hydrolysis and resolution as the (–)-cinchonidine salt (mp 119°–120° C., 119°–120° C.) which upon neutralization gave (–)-D-3-hydroxydecanoic acid ($[\alpha]_D = -21.4°$ C. (c 1.0, $CHCl_3$); lit. $[\alpha]D = -17.5°$) (Gilon, C., et al., *Tetrahedron Ltrs.* 40:3811–3814 (1979)). The final peptide was cleaved from the resin with TFA (50% in $CH_2Cl_2$, 30 min) and lyophilized from dioxane to yield the crude peptide (18). This was readily purified by reverse phase HPLC on a $C_{18}$ column using 0.1% aqueous TFA and a gradient of acetonitrile, with the resulting peptide being relyophilized from dilute anhydrous dioxane-HCl to yield (18)·HCl as a white solid in 25% overall yield based on resin substitution.

To complete the synthesis, cyclization reactions were carried out with a peptide concentration of 1 mM. Using DCC/HOBT in the presence of triethylamine, a single main product was obtained having a FAB mass spectrum consistent with the N-acylurea resulting from the O←→N peptide rearrangement of the intermediate O-acylisourea (Khorana, H. G., *Chem. Rev.* 53:145–166 (1953)) formed by reaction with DCC. Using BOP-Cl (Shute, R. E., et al., *J. Med. Chem.* 30:71–78 (1987)) and triethylamine in dioxane, the desired cyclic (19) (amino acid analysis, FAB mass spectrum) was obtained in 24% yield from 18 after HPLC purification. Debenzylation was carried out in methanol using ammonium formate and 10% Paladium on charcoal (Pd-C) (Anwer, M. K., et al., *Synthesis* 929–932 (1980)). Purification of the crude reaction product by HPLC yielded a white solid in 78% yield which had the expected amino acid analysis and FAB mass spectrum consistent with structure (1). Synthetic (1) was shown to be identical to natural viscosin both chromatographically (HPLC using a reverse-phase $C_{18}$ column with an aqueous acetonitrile system containing 0.1% TFA) and by NMR (300 MHz proton spectrum) thereby supporting structure (1) as the correct structural assignment for viscosin.

In summary, the successful synthesis of cyclic depsipeptides by solid-phase techniques is possible through the preparation of suitable branched fragments. Important aspects of this approach are the use of orthogonal Fmoc/Boc amino protection. Elaboration of the crucial ester branch point using unprotected hydroxyl-bearing amino acids is possible through the use of Pfp activation and a coupling order which minimizes O←→N acyl migration.

EXAMPLE 2

Preparation of Linear and Cyclic Viscosin Analogs

Methodology developed in the synthesis of viscosin was used to prepare analogs of viscosin designed to explore specific features of the molecule as they relate to various activities of viscosin.

Peptide Lactones

In the preparation of peptide lactones ring closure is most advantageously effected through amide bond formation rather than through esterification (Sheehan, J. C., et al., *J. Amer. Chem. Soc.* 95:875–879 (1973)). The linear depsipeptide fragments required for cyclization are usually synthesized by solution methods (Rinehart, K. L., et al., *J. Amer. Chem. Soc.* 109:6846–6848 (1987)), but solid-phase techniques have also been applied to the synthesis of these molecules (Gisin, B. F., et al., *J. Amer. Chem. Soc.* 91:2691–2695 (1969); Okada, K., et al., *Chem. Pharm. Bull.* 22:2136–2141 (1974)). The development of acid-sensitive resins which can be cleaved with trifluoroacetic acid (TFA) (Wang, S. S., *J. Amer. Chem. Soc.* 95:1328–1333 (1973)), acid-stable fluorenylmethyloxycarbonyl (Fmoc) amino protection (Carpino, L. A., et al., *J. Amer. Chem. Soc.* 92:5748–5749 (1970)) and pentafluorophenol (Pfp) active ester coupling (Kisfaludy, L., et al., *Synthesis* 325–327 (1983); Atherton, E., et al., *Tetrahedron* 44:843–857 (1988)) provided the basis for the solid-phase synthesis of viscosin. A key feature of the viscosin synthesis was its reliance on the preferential reactivity of Pfp esters with amines in the presence of alcohols (Kisfaludy, L., et al., in Peptides, Structure and Function, Proceedings of the Ninth American Peptide Symposium, Weber et al., eds., Pierce Chemical Co., Rockford, Ill. (1985)), for coupling of amino acids without hydroxyl group protection. In this manner the benzyl protected linear fragment having structure (18) was prepared by solid-phase techniques with the Ile ester branch point preformed and suitable for direct cyclization.

The four peptide lactones (1)–(4) which required the solid-phase synthesis of the corresponding linear fragments (18) and (20)–(22) were prepared using alkoxybenzyl alcohol resin (Wang, S. S., *J. Amer. Chem. Soc.* 95:1328–1333 (1973)) in a manner similar to that described above for the synthesis of viscosin. Coupling through Fmoc-D-Val was the same for each analog, using hydroxybenzotriazole (HOBT)/dicyclohexylcarbodiimide (DCC) (Paguet, A., *Can. J. Chem.* 60:976–980 (1982)) mediated coupling of Fmoc-protected amino acids (either obtained commercially or synthesized as crystalline solids using 9-fluorenylmethyloxy-succinimidyl carbonate (Fmoc-OSu) (Fuller, W. D., et al., Peptides structure and function, Proceedings of the Eighth American Peptide Symposium, Hruby and Rich, ed., Pierce Chemical Co., Rockford, Ill. (1983))). Epimerization of D-Thr (25) provided a ready source of D-allo-Thr ($[\alpha]_D$=−32.7°; $[\alpha]_D$ 2=−33.2°) (Hintzer, K., et al., *J. Org. Chem.* 47:3850–3854 (1982)). Although couplings of hydroxyl-bearing amino acids such as Thr and Ser are conducted without hydroxyl protection in solution synthesis where large excesses of amino acid are not required (Sheehan, J. C., et al., *J. Amer. Chem. Soc.* 95:875–879 (1973); Bodanzky, J. M., et al., *J. Amer. Chem. Soc.* 89:6753–6757 (1967)), side chain acylation has been reported for such reactions during solid-phase synthesis (Stewart, J. M., *The Peptides, Analysis, Synthesis and Biology,* Gross and Meienhofer, ed., Academic Press, New York, N.Y. (1981)). Relying on the selective reactivity of Pfp esters towards amines in the presence of alcohols (Kisfaludy, L., et al., Peptides, structure and function, Proceedings of the Ninth American Peptide Symposium, Weber, Hruby and Kopple, ed., Pierce Chemical Co., Rockford, Ill. (1985)), it was possible to safely couple amino acids with unprotected hydroxyls both on the incoming amino acid and on the resin. Synthesis of Fmoc-D-allo-Thr (26) and Fmoc-D-Thr were as described for the synthesis of Fmoc-L-Thr (Paguet, A., *Can. J. Chem.* 60:976–980 (1982)) with conversion to the corresponding Pfp esters by reaction with pentafluorophenol in the presence of DCC. (Synthesis of Fmoc-Thr-Pfp is possible directly from Thr by reaction with 9-fluoroenylmethyl pentafluorophenyl carbonate (Schon, I., et al., *Synthesis* 303 (1986))). Solid-phase coupling of both Fmoc-D-allo-Thr-Pfp (27) and Fmoc-D-Thr-Pfp (29) was achieved using 1.5 equivalents with reaction completion indicated by the Kaiser ninhydrin test (Kisfaludy, L., et al., in Peptides, Structure and Function, Proceedings of the Ninth American Peptide Symposium, Weber et al., eds., Pierce Chemical Co., Rockford, Ill. (1985)).

At this stage it is possible to construct the Boc-L-Ile branch point by esterifying the unprotected hydroxyl of either Fmoc-D-allo-Thr (for analogs (18), (21), and (22)) or Fmoc-D-Thr (analog (20)). However, this could result in significant side product formation during the subsequent piperidine catalyzed deblocking of the Fmoc group due to an O→N migration of Boc-L-Ile (Levy, D., et al., *Biochemistry* 9:3215–3222 (1970); Mauger, A. B., et al., *Int. J. Peptide Protein Res.* 30:481–488 (1987)). Since the reverse N→O migrations do not readily occur under the nonacidic conditions of the synthesis, the problem of acyl migration can be circumvented by initial acylation of nitrogen with subsequent esterification of the hydroxyl. Use of Pfp ester activation allowed this amidation to proceed in the presence of the unprotected hydroxyl. Therefore, the Fmoc-D-allo-Thr (Carpino, L. A., et al., *J. Amer. Chem. Socy.* 92:5748–5749 (1970)) was deblocked with piperidine and the resulting nitrogen acylated with the appropriate Pfp ester (Fmoc-OBzl-D-Glu-Pfp for peptides (18) and (21); octadecanoyl-Pfp for (22)). The remaining free hydroxyl of D-allo-Thr (Elliot, D. F., *J. Chem. Socy.*:62–68 (1950)) was then esterified with Boc-L-Ile using DCC in the presence of 0.1 equivalents of dimethylamino pyridine (DMAP) (Gilon, C., et al., *Tetrahedron Ltrs.* 40:3811–3814 (1979)).

Synthesis of analogs (18), (20) and (21) proceeded by a shortened piperidine deblock of Fmoc-OBzl-D-Glu (Schiffler, R. J., et al., *Amer. Med. Assoc.* 251:2983 (1984)). The reduction of deblock from 20 to 5 minutes was necessary to prevent the cyclization (Hubert, A. J., et al., *Helv. Chim. Acta* 46:1429–1445 (1963)) of OBzl-D-Glu to pyroglutamic acid. The orthoganol Boc/Fmoc protection scheme allowed the selective removal of the base labile Fmoc group, while maintaining the base insensitive Boc protection on the L-Ile. The synthesis was continued by coupling of Fmoc-L-Leu (Keierszenbaum, F., *Trop. Med. Parasit,* Mansfield ed., Marcel Dekker, New York (1984)) in the usual manner (DCC/HOBT) which was followed by piperidine-catalyzed Fmoc deprotection (20 minutes) and final acylation with either (−)-D-3-hydroxydecanoic acid (−), structure (23) (for analogs (18) and (20)), or decanoic acid (for analog (21)). Coupling of D-3-hydroxydecanoic acid was as the Pfp ester (24), with the 3-hydroxyl group unprotected. The acid was obtained by (−)-cinchonidine resolution (Cartwright, N.J., *Biochem. J.* 67:663–669 (1957)) of synthetic (±)-3-hydroxydecanoic acid [(35)-(12)]. The (±)-3-hydroxydecanoic acid itself (mp 55°–56° C.; 57° C.) was synthesized by the aldol condensation of lithium tert butyl acetate (Rathke, M. W., et al., *J. Amer. Chem. Soc.* 95:3050–3051 (1973)) with n-octyl aldehyde, followed by TFA hydrolysis of the resulting (±)-tert butyl acetyl-3-hydroxydecanoic acid.

Treatment of the resulting resins with 50% TFA in $CH_2Cl_2$ (30 minutes) resulted in simultaneous cleavage of the peptides from the support and removal of the Boc amino protection. The crude linear peptides (18) and (20)–(22) were purified by preparative high-pressure liquid chromatography (HPLC) and converted to HCl salts. Cyclizations were carried out in 1 mM dioxane solutions using BOP-Cl (Shute, R. E., et al., *J. Med. Chem.* 30:71–78 (1987); Diago-Mesguer, J., et al., *Synthesis:*547 (1980)) in the presence of triethylamine, giving crude benzyl protected cyclic peptides. The crude peptides were debenzylated directly using ammonium formate and 10% Pd-lkC (Anwer, M. K., et al., *Synthesis* 11:929–932 (1980)) in methanol (55°–60° C., 3 hr), giving after HPLC purification, the finished peptide lactones (1)–(4). Experience in the synthesis of viscosin had indicated that HPLC purification of intermediate benzyl protected lactones prior to debenzylation did not increase either the yield or quality of the final debenzylated peptide, and therefore it was deemed advantageous to omit this purification step. Preparative HPLC of peptides in this work was carried out on a scale of up to several hundred milligrams utilizing a 4.7×30 cm radial compression cartridge with $C_{18}$ packing and acetonitrile-$H_2O$ solvent system containing 0.1% TFA. The desired fractions could safely be taken to dryness using rotary evaporation at temperatures up to 60° C. without significant decomposition.

Linear Fragments

Because acyclic derivatives of cylic peptide antibiotics may retain the structure and/or activity of the parent compound (see, e.g., Maplestone, R., et al., *FEBS Letters* 326:95–100 (1993)), linear derivatives of viscosin were prepared. Synthesis of viscosic acid (5) and [D-Thr]-viscosic acid (6) utilized acid-sensitive alkoxybenzyl alcohol resin and Fmoc-chemistry in a manner similar to that used to make the linear fragments (18) and (20)–(22). Fmoc-L-Ile-alkoxybenzyl alcohol resin used as starting material was either purchased commercially or synthesized by reaction of commercially available Fmoc-L-Ile with alkoxybenzyl alcohol resin in the presence of dimethylformamide dineopentyl acetal (RT, 3 days) Albericio, F., et al., *Int. J. Peptide Protein Res.* 23:342–349 (1984)) followed by capping with benzoyl chloride providing 0.37 mmol/g resin substitution. Coupling of all amino acids beyond D-Val was as their Pfp esters with D-allo-Thr (for (5)), D-Thr (for (6)) and D-β-hydroxydecanoic acid (for both (5) and (6)) having their hydroxyl groups unprotected. The finished resins were cleaved with 50% TFA in $CH_2Cl_2$, evaporated to dryness under rotary evaporation and lyophilized from dioxane to yield benzyl-protected peptides as white solids which were debenzylated in the usual manner (ammonium formate, 10% Pd-C/MeOH, 55°–60° C.) and purified by preparative HPLC.

Preparation of linear fragment (7) was by solid-phase techniques starting from 4-methylbenzhydrylamine resin (Matsueda, G. G., et al., *Peptides* 2:45–50 (1981)). This was coupled twice with 2.5 equivalents Fmoc-OBzl-D-Glu using DCC, HOBT (3 hr) giving a negative Kaiser reaction. The resin was then deblocked with 50% piperidine in DMF for 5 min, washed and coupled with 2.5 equivalents of Fmoc-L-Leu (DCC, HOBT). A final piperidine deblock was followed by coupling with the Pfp ester of D-β-hydroxydecanoic acid to yield the finished resin which was dried. The resin was cleaved with anhydrous hydrogen fluoride (45 min, 0° C.) in the presence of anisole, extracted, lyophilized and purified by preparative HPLC.

Biological Considerations

That peptides can have dramatic effects on cell membranes is well-known. Cyclic peptides such as valinomycin (Brockmann, H., et al., *Chem. Ber.* 88:57–61 (1955)), the enniatins (Gaumann, E., et al., *Exper.* 3:202–203 (1947)), the polymixins (Horton, J. M., et al., in Antimicrobial Therapy, Ristuccia et al., eds., Raven Press, New York, N.Y. (1984), pp. 329–334; Storm, D. R., et al.,*Ann. Rev. Biochem.* 46:723–763 (1977)), and more recently EM 49 (Rosenthal, K. S., et al., *Antimicrob. Ag. Chem.* 12:665–672 (1977)) and the Echinocandins (Benz, F., et al., *Helv. Chim. Acta.* 57:2459–2477 (1974)) are thought to owe at least some of their antimicrobial activity to their ability to alter the integrity of cell membranes. Linear molecules can also cause lysis of cell membranes. Protein-size molecules such as diphtheria toxin (Donovan, J. J., et al., *Proc. Natl. Acad. Sci. USA* 78:172–176 (1981)) and cytolytic complement complexes (Bhakdi, S., et al., *Phil. Trans. R. Soc. Lond, B.* 306:311–324 (1984)) exert their lytic effects through association into transmembrane pores. This pore-forming mechanism is also an apparent explanation for small linear peptides such as the cercropins (from the humoral defense system of the giant silk moth *Hyalophora cecropia*) (Merrifield, R. B., et al., *Biochem.* 21:5020–5031 (1982)) and the magainins (Zasloff, M., et al., *Proc. Natl. Acad. Sci. USA* 85:910–913 (1988)) (also known as PGS (Giovannini, M. G., et al., *Biochem. J.* 243:113–120 (1987))) which are thought to form transmembrane α-helixes. Peptides studied to date as antichagaisic agents also apparently rely on membrane-active mechanisms (Mercado, T. I., et al., *Antimicrob. Agents Chemother.* 22:1051–1057 (1982); Jaynes, J. M., et al., *FASEB J.* 2:2878–2883 (1988)) (an exception being fibronectin fragment analogs which interfere with *T. cruzi* attachment to host cell membranes (Ouaissi, M. A., *Science* 234:603–607 (1986))).

Because *T. cruzi* is a unicellular organism whose life cycle intimately depends on the interaction of its plasma membrane with host structures, it might be expected that the membrane is highly developed and selective in its actions. Studies conducted on the membrane composition of *T. cruzi* have shown that the fatty acid composition is unique, ranging up to 22 carbons with linoleic acid ($C_{18}\Delta^{12,15}$) being the major fatty acid, even though other fatty acids may predominate in the extracellular medium (Timm, S. L., *Comp. Biochem. Physiol.* 71B:397–402 (1982)). There is a requirement for stearic ($C_{18}$) acid when grown in defined media (Bone, G. J., et al., *J. Gen. Microbiol.* 31:261–266 (1963)), and while fatty acids of chain length 12 and 16 carbons are toxic to *T. cruzi*, and 18 carbon linoleic acid is not toxic even in molar concentrations. It is also known that long-chain fatty acids are extremely toxic to other trypanosomes, with toxicity varying widely among closely related fatty acids (Cunningham, L. A., et al., *J. Gen. Microbiol.* 70:491–496 (1972); Balis, J., *Revue d'Elevage et de Medicine Veterinaire des Pays Tropical* 19:351–356 (1966)). a lytic effect against *T. cruzi* has been observed in a long-chain fatty acid fraction from the marine alga *Ulva lactuca* (Cunningham, L. A., et al., *J. Gen. Microbiol.* 70:491–496 (1972)), and cod-liver oil, which is enriched in long-chain fatty acids, has been shown to have a suppressive effect on some trypanosome infections in mice (Godfrey, D. G., *Exp. Parasitol.* 7:255–268 (1958)).

As seen with antitrypanosomal factors derived from *Pseudomonas fluorescens* (Mercado, T. I., et al., *Antimicrob. Agents Chemother.* 22:1051–1057 (1982)), the most readily apparent effect of viscosin on *T. cruzi* is to cause disruption of the cell membrane. It can be speculated that viscosin is acting as either a cell-specific detergent or as an ionophore, a property of other cyclic peptides (Tosteson, D. C., *J. Gen. Physiol.* 50:2513–2525 (1967)). Viscosin along with a number of other cyclic peptide antibiotics has a fatty acyl portion (Vining, L. C., et al., *Can. J. Chem.* 40:1579–1584 (1962)), and the fatty acid portions of antibiotics such as EM49 and the polymyxins have been shown to be extremely important to their activity perhaps by aiding in insertion of the molecules into the lipid membranes (Storm, D. R., et al., *Ann. Rev. Biochem.* 46:723–763 (1977)). Since *T. cruzi* is quite specific as to the fatty acids it will incorporate (Timm, S. L., et al., *Comp. Biochem. Physiol.* 71B:397–402 (1982)), it may be possible to utilize this specificity as a means of increasing selectivity and toxicity of peptide analogs towards *T. cruzi*.

Since there has been no structure-activity work reported on the efficacy of viscosin towards trypanosomes such as *T. cruzi,* a series of analogs were synthesized in an effort to increase specificity and toxicity towards *T. cruzi* and to decrease the synthetic complexity. Therefore, analogs (3) and (2) were prepared respectively with the D-β-hydroxydecanoic acid replaced by the simpler decanoic acid and the D-allo-Thr replaced by the more readily available D-Thr. Analog (4), which replaces the D-β-hydroxydecanoyl-L-Leu-D-Glu side chain with a simple $C_{18}$ amide, was designed to increase affinity and uptake by *T. cruzi* by taking advantage of the unique role $C_{18}$ acids apparently occupy in the *T. cruzi* membrane. In principle, this analog relies on the side chain to direct and anchor the peptide in the trypanosome membrane, with lytic activity residing potentially in the peptide ring. It should be noted that in viscosin itself the chain length from the γ-carboxyl of D-Glu to the end of the acyl side chain is 18 units. The possibility exists, however, that antibiotic activity of viscosin resides principally in the side chain, and not in the ring. Such antibiotic activity has been observed in other small fatty acylated mono- and dipeptides (Gaur, R. K., et al., *Ind. J. Chem.* 27B:405–408 (1988); Volger, K., et al., *Helv. Chim. Acta.* 47:526–544 (1964)). Therefore, side chain fragment (7) was prepared to examine this possibility. Finally, linear analogs, viscosic acid (5) and [D-Thr$^{7}$]-viscosic acid (6) were prepared to examine the activity of ring-opened derivatives.

Chemical Methods

Melting points were determined on a MelTemp melting point apparatus and are uncorrected. Fast atom bombardment mass spectra (FAB MS) and chemical ionization mass spectra (CIMS) were determined either at Oneida Research Services, Inc. (Whitesboro, N.Y.), the Mass Spectrometry Facility of the University of Maryland Department of Chemistry (College Park, Md.), or at the Middle Atlantic Mass Spectrometry Laboratory (The Johns Hopkins University, Baltimore, Md.). Ultraviolet spectroscopy was performed on a Hewlett Packard Model 8451A spectrometer. Optical rotations were recorded on a Perkin-Elmer 241MC polarimeter. High pressure liquid chromatography (HPLC) was performed using a Waters Division of Millipore LC 3000 solvent delivery system equipped with a Rheodyne 7010 injector, a Model 381 variable wavelength detector, a Model 740 data module, and for preparative work, either a PrepPak 1000 radial compression module equipped with a μBondapak $C_{18}$ 4.7×30 cm (15–20μ particle size) cartridge (run at 60 mL/min) or a YMC $C_{18}$ column (15–20μ particle size, 120 Å pore; 20 mm×250 mm) run at 20 mL/min. Flash chromatography was performed using EM Kieselgel 60, 230–400 mesh. Substitution of alkoxybenzyl alcohol resins was measured by UV absorbance at 267 nm (e=18,950 (Chang, C., et al., *Int. J. Pept. Res.* 15:59–66 (1980))) following cleavage with 50% trifluoroacetic acid (30 min). Amino acid analysis was determined by samples hydrolyzed in 6 N HCl at 110° C. for 22 hours and separated by ion exchange in a St. John's Associates analyzer. Combustion analysis was performed at Galbraith Laboratories, Inc. (Knoxville, Tenn.) and were within 0.4% of theoretical values unless otherwise indicated.

Synthesis of Specific Viscosin Analogs and Components Thereof

(±)-3-Hydroxydecanoic Acid [(±)-(23)]

A solution of lithium diisopropylamide was prepared by diluting 125 mL (200 mmol) of 1.6 M n-butyl lithium in hexane with 300 mL of toluene, and stirring with 20.2 g (200 mmol) of diisopropylamine for 30 min at 0° C. This was cooled to −78° C., stirred with 23.2 g (200 mmol) of tert-butyl acetate (1 hr), then at 0° C. (1 hr). A total of 20.5 g (160 mmol) of octyl aldehyde was added, then the reaction was brought to RT and stirred 1 hr. The reaction was quenched by addition of 10% HCl and solvent removed by rotary evaporation under reduced pressure. The resulting yellow oil was treated with neat TFA (150 mL, 30 min, RT), then evaporated to dryness and partitioned between dilute aqueous HCl and $CH_2Cl_2$. The combined organic phase was washed with saturated NaCl, dried ($MgSO_4$) and taken to dryness by rotary evaporation. Crystallization of the resulting reddish oil from hexane yielded (±)-12 as white crystals (20.0 g, 67% yield), mp 55°–57° C. (lit. 57° C.). CIMS ($NH_3$): m/z 206 ($M+NH_4^{30}$ ).

(−)-D-3-Hydroxydecanoic Acid [(−)-(23)]

(±)-3-Hydroxydecanoic acid (23) 20.0 g (106 mmol) was resolved as the (−)-cinchonidine salt by previously-described procedures (Cartwright, N.J., *Biochem. J.* 67:663–669 (1957)). After seven crystallizations from $CCl_4$ and two from ethyl acetate (all crystallizations were carried out at RT), a total of 6.2 g of (−)-cinchonidine(−)-3-hydroxydecanoate salt was obtained, mp 121°–122° C. (mp 119°–120° C.). The salt was partitioned between 0.5 N HCl (100 mL) and $CH_2Cl_2$ (3×100 mL) and the combined organic layers were washed with saturated NaCl (2×100 mL), dried ($MgSO_4$) and evaporated to an oil which crystallized. Recrystallization from hexane yielded (−)-(23) as white crystals (2.3 g 23%), mp 46°–47° C., $[\alpha]_D$=−21.4° (c 1.0, $CHCl_3$) (mp 47° C., $[\alpha]_D$=17.5° (c 0.9, $CHCl_3$)).

Pentafluorophenyl D-3-hydroxydecanoate (24)

A solution of (−)-3-hydroxydecanoic acid (−)-(23) (3.76 g, 20 mmol), pentafluorophenol (4.04 g, 22 mmol) and dicyclohexylcarbodiimide (4.32 g, 21 mmol) in $CH_2Cl_2$ was stirred at RT for 3 hr. The mixture was then cooled in ice, dicyclohexylurea was removed by filtration and the filtrate evaporated to a colorless oil. Purification by silica gel flash chromatography (5×25 cm i.d. column, $CH_2Cl_2$) yielded product (24) as a colorless oil which crystallized (6.50 g, 92%) mp 48°–49° C. CIMS ($NH_3$); m/z 372 ($M+NH_4^+$). Anal. ($C_{16}H_9F_5O_3$) C, H.

D-allo-Thr (25)

Synthesis of D-allo-Thr (25) was by known procedure (Elliot, D. F., *J. Chem. Soc.* 62–68 (1950)) starting from D-Thr (54% overall yield, $[\alpha]_D$=−32.7° (c1.0, 1N HCl); and $[\alpha]_D$−−33.2° (c 1.0, 1 N HCl)) (Hintzer, K., et al., *J. Org. Chem.* 47:3850–3854 (1982)).

Preparation of Fmoc Amino Acids

All Fmoc amino acids were synthesized from the corresponding free amino acids by the following general procedure. To a solution of D-allo-Thr (25) (1.62 g, 13.6 mmol) and NaHCO$_3$ (3.4 g, 41 mmol) in H$_2$O (60 mL) was added a solution of Fmoc-OSu (4.58 g, 13.6 mmol) in dioxane (60 mL) and the turbid reaction mixture stirred at RT overnight. The mixture was then diluted with H$_2$O, acidified to pH≦4 by addition of 37% HCl and extracted with ethyl acetate (3×100 mL). The combined ethyl acetate extracts were washed with saturated NaCl (2×100 mL), dried (MgSO$_4$) and taken to dryness by rotary evaporation to give a colorless oil which was crystallized from ethyl acetate/hexane, yielding Fmoc-D-allo-Thr (26) as white crystals (3.7 g, 80%), mp 152°–153° C. Anal. (C$_{19}$H$_{19}$NO$_5$) C, H, N.

Preparation of Pfp Esters of Fmoc Protected Amino Acids

The following is a typical procedure used to prepare Pfp esters of Fmoc protected amino acids: to a solution of Fmoc-D-allo-Thr (26) (3.41 g, 10.0 mol) and pentafluorophenol (2.29 g, 12. 0 mmol) in dioxane (40 mL) was added a solution of DCC (2.06 g, 10.0 mmol) in dioxane (10 mL) and the reaction stirred at RT overnight. The mixture was then cooled in ice, dicyclohexyl urea removed by filtration, and the filtrate evaporated to a colorless oil which crystallized. Trituration with hexane yielded product (27) as 5.00 g (100%) of white solid, mp 142°–144° C. Anal. (C$_{25}$H$_{18}$F$_5$NO$_5$) C, H, N.

Fmoc-D-Val-L-Leu-OBzl-D-Ser-L-Leu-OBzl-D-Ser-Alkoxybenzyl Alcohol Resin (28)

Solid-phase synthesis employed manual techniques using apparatus as previously described (Stewart, L. M., et al., Pierce Chemical Co., Rockford, Ill. (1984)). Mixing of resin was by a rocking motion of 28 cycles per min with solvent used in the proportion of 5 mL/g resin. Starting alkoxybenzyl alcohol resin 10.0 g (0.65 mmol-OH/g resin; either synthesized from choromethyl resin (Wang, S. S., *J. Amer. Chem. Soc.* 95:1328–1333 (1973)) or purchased from commercial sources) was washed with DMF (4x), CH$_3$Cl$_2$ (4x) then coupled with Fmoc-OBzl-D-Ser 19 (6.78 g, 16.25 mmol), DCC (3.35 g, 16.25 mmol), pyridine (1.28 g, 16.25 mmol) and dimethylamino pyridine (0.08 g, 0.65 mmol) in 50 mL DMF (3 hr), giving a resin substitution of 0.36 mmol/g. The coupling was repeated identically resulting in a substitution of 0.66 mmol/g. The resin was washed with DMF and CH$_2$Cl$_2$ (3 x each) then capped by treating with benzoyl chloride (1.4 g, 10 mmol) and pyridine (790 mg, 10 mmol) in 50 mL CH$_2$Cl$_2$ (30 min). Coupling cycles were then begun as follows: The resin was washed with DMF (3 x); CH$_2$Cl$_2$ (3 x); deblocked with 50% piperidine in DMF (50 mL, 20 min); washed with DMF (3 x) and CH$_2$Cl$_2$ (3 x) then coupled with 2.5 equivalents each of Fmoc amino, DCC and HOBT in 50 mL DMF. After 3 hr the resin was monitored for unreacted amino groups by the Kaiser test (Kaiser, R. L., et al., *Anal. Biochem.* 34:595–598 (1970)). If necessary, coupling was repeated in an identical manner to achieve a negative Kaiser reaction. Following completion of the coupling process, the resin was washed, deblocked and coupled with the next amino acid as indicated above. The results of several synthesis indicated that while single couplings were usually adequate for Fmoc-OBzl-D-Ser and Fmoc-D-Val, multiple couplings were required for Fmoc-L-Leu approximately 50% of the time. Coupling was continued through Fmoc-D-Val, then the resin was removed, dried and portions used for further elaboration as indicated below.

Viscosin Linear Fragment (18)

A total of 4 g (3 mmol) of resin (28) was washed with DMF (3×20 mL), deblocked (20 mL of 50% piperidine in DMF, 20 min), washed (6×20 mL DMF) and reacted with 1.5 equivalents (1.52 g, 3 mmol)l of Fmoc-D-allo-Thr-Pfp ester (27) in 20 mL DMF. Following completion of coupling (1.5 hr as indicated by a negative Kaiser test), the resin was washed with DMF and CH$_2$Cl$_2$ (3×20 mL each), deblocked with piperidine as before and coupled to completion with 1.5 equivalents of Fmoc-OBzl-D-Glu-Pfp ester (1.88 g, 3 mmol) in 20 mL DMF (1.5 hr). The resin was then washed (3×10 mL each DMF, CH$_2$Cl$_2$) and esterified directly by coupling twice (2 hr per couple) with 2.5 equivalents Boc-L-Ile (1.16 g, 5.0 mmol), DCC (1.03 g, 5.0 mmol), pyridine (395 mg, 5.0 mmol) and DMAP (61 mg, 0.5 mmol) in DMF (20 mL). (NOTE: There is no piperidine deblock before this esterification.) The resin was washed and subjected to an abbreviated piperidine deblock (50% piperidine in DMF, 5 min) before coupling with 5 equivalents of Fmoc-L-Leu (2.31 g, 10 mmol) and DCC (2.06 g, 10 mmol). Coupling was complete after 3 hr and the resin was washed, deblocked as previously described with piperidine (5 min) and reacted with D-3-hydroxydecanoic acid-Pfp ester 24 (750 mg, 2.1 mmol) in 10 mL of CH$_2$Cl$_2$ (4 hr). The finished resin was cleaved with 50% TFA in CH$_2$Cl$_2$ (20 mL, 30 min) and the product evaporated to dryness and lyophilized from dioxane to yield 1.2 g crude (5). Purification by preparative HPLC was conducted in two batches (PrepPak 1000 radial compression cartridge; 0.1% aqueous TFA with a linear gradient of acetonitrile 0–70% in 60 min at a flow of 60 mL/min) yielding, after lyophilization, purified (18) as a white solid (740 mg, 26% yield based on resin substitution). FAB MS m/z:1414(M+1).

[D-Thr $^6$]-Viscosin Linear Fragment (20)

Synthesis of (20) was accomplished in a manner similar to that used to prepare linear viscosin fragment (18), except that Fmoc-D-Thr-Pfp (29) was used rather then Fmoc-D-allo-Thr-Pfp (27). Starting with 0.8 mmol of resin (28), 635 lmg of crude peptide was obtained, from which was obtained 139 mg (12% yield based on resin substitution) of purified (20) following HPLC purification as described for (18). FAB MS m/z: 1415 (M+1); 1453 (M$^{+K+}$).

Deshydroxy-Viscosin Linear Fragment (21)

Synthesis of (21) was accomplished in a manner similar to that used to prepare linear viscosin fragment (18), except that pentafluoro decanoate was used rather then pentafluoro D-3-hydroxydecanoate. A 1 mmol synthesis produced 535 mg (38%) of purified (21) following preparative HPLC as described for (18). FAB MS m/z: 1398 (M+1).

Octadecanoyl Linear Fragment (22)

Synthesis of (22) on a 1 mmol scale was accomplished in a manner similar to that used to prepare linear viscosin fragment (18) through the coupling of Fmoc-D-allo-Thr. At this point the resin was deblocked with piperidine and washed in the usual manner. A mixture of stearic acid (568 mg. 2.0 mmol), pentafluorophenol (442 mg, 2.4 mmol) and DCC (412 mg, 2.0 mmol) in CH$_2$Cl$_2$ (20 mL) was stirred at RT for 30 min, then added to the deblocked resin. After 3 hr the reactiob had failed to go to completion as indicated by a Kaiser test. Recoupling with 550 mg (1.0 mmol) of stearic anhydride in CH$_2$Cl$_2$ (20 mL) in the presence of triethylamine (200 mg, 2 mmol) gave a negative Kaiser test after 20 min. The resin was washed and coupled twice (3 hr each) with 1.15 g (5 mmol) of Boc-L-Ile 1.03 g (5 mmol) of DCC, 63 mg (0.5 mmol) of DMAP and 400 mg (5 mmol) of pyridine in DMF (20 mL). The resulting resin was cleaved with 50% TFA in $CH_2Cl_2$ (30 min) and lyophilized from dioxane as previously indicated. Preparative HPLC (PrepPak 1000 cartridge system) of the resulting crude peptide was performed. A total of 840 mg (71%) of purified (22) was obtained as a white solid. FAB MS m/z: 1179 (M+1), 1201 (M+Na$^+$), 1224 (M+2Na$^+$).

Viscosin (1)

A total of 200 mg (140 μmol) of linear (18) was dissolved in 20 mL of dry dioxane (4 Å sieves), 20 dps of 4N·HCl dioxane was added and the solution taken to dryness under

D-Lys-Viscosin (39)

Synthesis of D-Lys-viscosin (39) required the preparation of Nα-Fmoc-Nε-Boc-D-Lys, which was obtained from commercially available Nε-Boc-D-Lys by acylation with Fmoc-OSu/aq. $NaHCO_3$/dioxane. The coupling order in the solid-phase synthesis replaced D-allo-Thr with the Lys derivative. Coupling of Boc-L-Ile was omitted. Resin cleavage yielded crude peptide as a white solid which was purified by preparative HPLC, yielding 600 mg (50% yield based on resin substitution) of purified linear

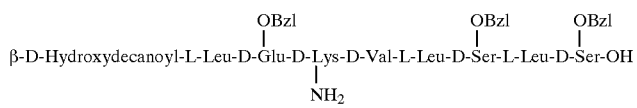

rotary evaporation (40° C.). The process was repeated, giving a residue which was derived under high vacuum. This was suspended in dry dioxane (140 mL) and stirred with 43 mg (168 μmol) BOP-Cl and 283 mg (2.8 mmol triethylamine (48 hr)). The cloudy reaction mixture was taken to dryness by rotary evaporation (40° C.), then resuspended in methanol (50 mL) and stirred at 55° C. with 880 mg (14 mmol) ammonium formate and 300 mg 10% Pd·C (5 hr). Removal of Pd·C by filtration and rotary evaporation of the filtrate gave crude viscosin as a colorless resin which was purified by preparative HPLC (PrepPak 1000 cartridge system). A total of 45 mg (29%) of purified (1) was obtained as a white solid. FAB LMS m/z: 1126 (M+1), 1148 (M+Na$^+$), 1164 (M+K$^+$). Addition of CsCl produced a base peak of 1258 (M+Cs$^+$).

[D-Thr $^6$]-Viscosin (2)

Cyclization of 83 μmol of linear (20) was in a manner similar to that indicated for cyclization of linear viscosin fragment (18). After reacting with 1.2 equivalents of BOP-Cl for 24 hr, an additional 1.2 equivalents of BOP-Cl was added and the cyclization continued for 44 hr. The crude reaction mixture was evaporated to dryness, debenzylated as indicated for (1), and purified twice by preparative HPLC giving 10 mg (11% yield) of purified (2). FAB MS m/z: 1127 (M+1), 1149 (M+Na$^+$).

Deshydroxy Viscosin (3)

Cyclization and subsequent debenzylationb of linear (21) was performed on a 150 μmol scale in a manner similar to that indicated for cyclization of linear viscosin fragment (18). The resulting crude peptide lactone was purified by preparative HPLC (PrepPak 1000 cartridge system). A total of 86 mg (52%) of purified (3) was obtained as a white solid. FAM MS m/z: 1110 (M+1), 1148 (M+K$^+$).

Dbu-Viscosin (37)

Synthesis of 2,4-diaminobutyric (Dbu) acid viscosin (37) was accomplished in a manner similar to that used to prepare viscosin (1), except that a linear intermediate was constructed on an alkoxybenzyl resin starting with Fmoc-L-Ile rather than Fmoc-OBzl-D-Ser and 4-N-Boc-2-N-Fmoc-2,4-diaminobutyric acid is used instead of Fmoc-D-allo-Thr.

Cyclization of this compound produced benzyl protected [D-Lys]-viscosin (38). Debenzylation of (38) yields D-Lys-Viscosin (39).

D-Orn-Viscosin (41)

Synthesis of D-Orn-viscosin (41) required the preparation of Nα-Fmoc-Nδ-Boc-D-ornithine, which in turn required Nδ-Boc-D-ornithine. The enantiomeric Nδ-Boc-L-ornithine has been previously prepared (Rosowsky, A., et al., *J. Med. Chem.* 29:655–660 (1986)) by reaction of the bis(L-ornithinato)copper(II) complex with BOC-ON in aq. dioxane in the presence of a tertiary amine base. The resulting Nδ-Boc-L-ornithine is liberated by treatment with EDTA and extraction in an alcohol containing organic phase. Starting with D-ornithine, a product was obtained in 19% yield as a white solid. This was then treated with Fmoc-Osu in aqueous $NaHCO_3$/dioxane (overnight) to yield an oily product which was purified first by silica gel flash chromatography then by preparative HPLC ($C_{18}$) to yield an essentially pure white solid.

Octadecanoyl Viscosin (4)

Cyclization (24 hr reaction time) and debenzylation of 300 μmol of linear 22 was performed as indicated for the preparation of viscosin (1). The crude product was purified twice by preparative HPLC using the PrepPak 1000 cartridge system giving 24 mg (10%) of purified (4) as a white solid. FAB MS m/z: 980 (M+1).

Viscosic Acid (5)

A total of 2.0 g of alkoxybenzyl alcohol resin (0.6 mmol —OH/g resin) was placed in a manual synthesis shaker and washed (3×10 mL DMF; 3×10 mL $CH_2Cl_2$) then shaken for 3 days with a solution of Fmoc-L-Ile (1.76 g, 5 mmol) and dimethylformamide dineopentyl acetal (1.15 g, 5 mmol) in $CH_2Cl_2$ (10 mL). The resin was then washed, capped (benzoyl chloride (2.4 g, 17 mmol) and pyridine (1.7 g, 21 mmol) in 10 mL $CH_2Cl_2$, 20 min) and dried, giving a substitution of 0.37 mmol/g resin. Synthesis was continued through Fmoc-D-Val as previously indicated for the synthesis of linear viscosin fragment (18). The resin was washed, dried and divided into two equal 0.37 mmol portions. One portion was removed for use in the synthesis of fd[D-Thr$^7$]-viscosic acid (6). The remaining 0.37 mmol was continued through Fmoc-OBzl-D-Glu as previously indicated for the synthesis of linear viscosin fragment (18). At this point the resin was deblocked with piperidine (50% in DMF, 5 min)

and coupled for 6 hr with a solution of Fmoc-L-Leu-Pfp [formed by reaction of Fmoc-L-Leu (480 mg, 0.92 mmol), DCC (190 mg, 0.92 mmol) and pentafluorophenol (203 mg, 1.10 mmol) in 10 mL DMF (30 min)]. Synthesis was completed by piperidine deblock (20 min) and coupling for 2 hr with pentafluorophenyl D-3-hydroxydecanoate (24) (330 mg, 0.93 mmol). The product was cleaved with 50% TFA (30 min), evaporated to dryness and lyophilized from dioxane to yield 670 mg of yellow resinous solid. This was debenzylated as indicated for the synthesis of viscosin (1), and purified by preparative HPLC (PrepPak 1000 cartridge system). A total of 144 mg (34%) of purified (5) was obtained as a white solid. FAB MS m/z: 1166 (M+Na$^+$), 1182 (M+K$^+$).

[D-Thr$^7$]-Viscosic Acid (6)

The 0.37 mmol of Fmoc-D-Val-resin from the above synthesis of viscosic acid was treated in a manner identical to that described for the synthesis of viscosic acid (5), except that Fmoc-D-Thr-Pfp ester (29) was used rather then Fmoc-D-allo-Thr-Pfp ester (27). A total of 575 mg of crude benzyl protected peptide was obtained, which after debenzylation as for viscosic acid yielded 290 mg of crude product. Purification by preparative HPLC as indicated for viscosic acid yielded purified (6) as 41 mg (10%) of white solid.

D-3-Hydroxydecanoyl-L-Leu-D-Glu-Amide (7)

A total of 2.0 g of 4-methylbenzhydryl amine resin (0.53 mmol N/g resin; resin was in the HCl salt form) was placed in a manual synthesis shaker and washed with DMF (3×10 mL), neutralized with piperidine (50% in DMF, 20 min) and washed (3×30 mL DMF; 3×20 mL CH$_2$Cl$_2$). The resin was then coupled quantitatively (Kaiser test) with two Fmoc-OBzl-D-Glu couples [1.22 g (2.65 mmol) Fmoc-OBzl-D-Glu, 550 mg (2.65 mmol) DCC and 400 lmg (2.65 mmol) HOBT in 20 mL DMF, 3 h]. The resin was then subjected to a 5 min piperidine deblock and coupled with Fmoc-L-Leu [1.87 g (5.3. mmol) Fmoc-L-Leu, 1.10 g (5.3 mmol) DCC and 800 mg (5.3 mmol) HOBT in 20 mL DMF, 2 h]. The resin was washed, deblocked (5min, 50% piperidine) and coupled with pentafluoro-D-3-hydroxydecanoate (24) (940 mg, 2.66 mmol) in DMF (20 mL) for 2 hr. The resulting resin was washed, dried and treated with 20 mL of anhydrous HF in the presence of 1.8 mL of anisole (0° C., 45 min). The HF was distilled off and the resin extracted with glacial acetic acid and lyophilized to yield crude (7) as 185 mg white solid. Purification by preparative HPLC (PrepPak 1000 cartridge system) gave a total of 100 mg (22%) of purified (7) was obtained as a white solid. FAB MS m/z: 429 (M+Na$^+$).

EXAMPLE 3

Preparation of Crown Ether Analogs of Viscosin

In a continuationb of the work with analogs, additional analogs have been prepared which replace the peptide lactone ring of viscosin with a crown ether.

Synthesis

The synthesis of crown ether analogs (10)–(16) began with commercially available benzo-15-crown-5. For attachment of side-chain moieties, the aryl ring was functionalized first by nitration to the mononitrobenzo-15-crown-5 (30) using 70% HNO$_3$ in AcOH/CHCl$_3$ (94% yield; mp 95°–96° C.; CIMS m/z 314 (M+1); 3.91 (M+2K$^+$): mp 84°–85° C.) (Ungaro, R., et al., J. Amer. Chem. Soc. 98:5198–5202 (1976)). Subsequent reduction of the nitro group to an amine, giving 4'-aminobenzo-15-crown-5 (31), was conducted with ammonium formate/10% Pd·C (Anwer, M. K., et al., Synthesis 11:929–932 (1980)) in modification of a previous synthesis (Ungaro, R., et al., J. Amer. Chem. Soc. 98:5198–5202 (1976)). Although the free amine has been reported as a solid (mp 73°–74° C.) (Ungaro, R., et al., J. Amer. Chem. Soc. 98:5198–5202 (1976)), in our hands it proved to be an oil which rapidldy darkened over time. The amine was stored by conversion to the hydrochloride salt (HCl/dioxane) giving a white to light blue solid which was stable at room temperature (single peak on reverse phase HPLC, no color change). For subsequent reactions, the hydrochloride salt was converted to the free base immediately prior to use by partitioning between aq. NaHCO$_3$ and CH$_2$Cl$_2$ and evaporating to dryness.

The preparation of peptide analogs (10)–(13) utilized amino acids bearing butyloxycarbonyl (Boc) amino protection with carboxyl activation through in situ generated pentafluorophenyl (Pfp) esters (Kisfaludy, L., et al., Synthesis 325–327 (1983)). Intermediate mono- and dipeptides (32) and (33) were isolated and characterized before being subjected to amino deprotection using 25% trifluoroacetic acid (TFA) in CH$_2$Cl$_2$. Preparation of analogs (10) and (11) required the acylation of dipeptide H-L-Leu-OBzl-D-Glu-crown ether (deprotected 33) with D-3-hydroxydecanoic acid Pfp ester (24). The selective acylation of the Leu amino group in the presence of the unprotected hydroxyl on the 3-hydroxydecanoic acid is an example of the differential reactivity of Pfp esters towards amines in the presence of alcohols (Kisfaludy, L., et al., Peptides, Structure and Function, Proceedings of the Ninth American Peptide Symposium, Weber, Hruby and Kplle ed., Pierce Chemical Co., Rockford, Ill. (1985)). Debenzylation of analogs (10), (12) and (14) was carried out catalytically using ammonium formate/10% Pd·C (Anwer, M. K., et al., Synthesis 11:929–932 (1980)).

Synthesis of 4-carboxyoctadecanoyl derivatives (14) and (15) required the preparation of benzyl-4-carboxyoctadecanoic acid (8). A synthetic route to (8) was employed which utilized the malonic ester synthesis of intermediate adduct (34). Although the reported preparation of a series of di-tert butylalkylmalonates utilized a two-fold excess of malonic ester and 1.5 equivalents of NaH relative to alkylbromide (Fonken, G. S., et al., J. Amer. Chem. Soc. 74:831–833 (1952)), the present synthesis of (34) used equal quantities of all reactants without apparent problems of serious dialkylation. Structural confirmation of (34) was aided by TFA removal of t-butyl groups to provide known tetradecylmalonic acid (Asano, M., et al., J. Pharm. Soc. Jpn. 61:220–228 (1941); Chargaff, E., Chem. Ber. 65B:745–754 (1932)). Adduct (34) was subjected to a Michael addition with benzyl acrylate to give (35). While a study on the addition of alkylmalonic esters (with alkyl substituents ranging from up to 16 carbons) to acrylic esters has reported the use of catalytic quantities of base (Floyd, D. E., et al., J. Org. Chem. 16:882–886 (1951)), care must be taken to exclude extraneous sources of acidic protons which can terminate the catalysis. The crude addition product was treated with TFA, removing the Boc groups to yield diacid (36) whikch provided fine white crystals from hexane. The decarboxylation of diacid (36) to final product (8) was achieved using 1% aq. DMF at 100°–105° C. overnight in a manner similar to the reported decarboxylation of β-keto esters (Paine, J. B., et al., J. Org. Chem. 41:3857–3860 (1976)). Purification by silica gel flash chromatography and crystallization from acetonitrile gave pure crystalline (8).

Biological Considerations

It has long beend known that certain antibiotics, particularly those of a peptide nature, are capable of increasing the alkali ion permeability of both synthetic and natural lipid membranes (Pressman, B. C., et al., *Proc. Natl. Acad. Sci. USA* 58:1949–1957 (1967); Tosteson, D. C., *Fed. Proc.* 27:1269–1277 (1968)). Of particular importance in this class of substances are the peptide lactones of which valinomycin and the enniatins are well-studied (Shemyakin, M. M., et al., *Experentia* 19:566 (1963)). Studies of valinomycin, enniatins and related peptides have provided some answers to questions regarding the relationship of peptide structure to their behavior towards membranes.

The possibility exists that the ring portion of viscosin serves as an ionophore in a structurally nonspecific manner. Selectivity and specificity could be imparted by the side chain, which could offer membrane-directed properties. If this were indeed the case,d then structurally simple crown ethers, which are well-characterized ionophoric agents (Pedersen, C. J., *Science* 241:536–540 (1988)), could possibly be substituted for this portion of the molecule. The antimicrobial action of crown ethers is known (Yagi, K. et al., *J. Inclusion Phenom.* 2:179–184 (1984)) and certain aspects of valinomycin SAR have been examined by crown ether mimetics having small peptide side chains (White, B. D. et al., *J. Org. Chem.* 54:937–947 (1989)).

Replacement of the peptide ring of viscosin with a crown ether would result in substantial reduction of synthetic complexity. Biological selectivity would then reside with the attached side chain. A series of crown ether analogs are possible, incorporating those side chain functionalities which are examined in analogs (10)–(16). Benzo-15-crown-5 ethers (11) and (13) bear the side chains of viscosin (1) and deshydroxy viscosin (3), respectively.

Chemical Methods

Melting points were determined on a MelTemp melting point apparatus and are uncorrected. Fast atom bombardment mass spectra (FAM MS) and chemical ionization mass spectra (CIMS) were determined either at Oneida Research Services, Inc. (Whitesboro, N.Y.) or at the Mass Spectrometry Facility of the University of Maryland Department of Chemistry (College Park, Md.). High-pressure liquid chromatography (HPLC) was performed using a Waters Division of Millipore LC 3000 solvent delivery system equipped with a Rheodyne 7010 injector, a Model 381 variable wavelength detector, a Model 740 data module, and for preparative work, a Water's PrepPak 1000 radial compression module equipped with a Bondapak $C_{18}$ 4.7×30 cm (15–20$\mu$ particle size) cartridge (run at 60 mL/min). Column chromatography was performed using EM Kieselgel 50, 230–400 mesh. Combustion analysis were performed at Galbraith Laboratories, Inc. (Knoxville, Tenn.) and were within 0.4% of theoretical values unless otherwise indicated.

Synthesis

15-[[N-[(1,1-dimethylethoxy)carbonyl]-O-(phenylmethyl)-D-glu-tamyl]amino]-2,3,5,6,8,9,11,12-octahydro-1,4,7,10,13-benzopentaoxacyclopentadecin or 4'-[(Boc-OBzl-D-Glu)amino]benzo-15-crown-5 (32)

A solution of Boc-OBzl-D-Glu-Pfp ester was prepared by reacting Boc-OBzl-D-Glu (680 mg, 2.0 mmol), pentafluorophenol (552 mg, 3.0 mmol) and dicyclohexylcarbodiimide (DCC) (412 mg, 2.0 mmol) in 10 mL of $CH_2Cl_2$ (1½ hr, RT). Dicyclohexylurea side product was removed by filtration. A total of 2.0 mmol of 4'-aminobenzo-15-crown-5 (31) (obtained from the corresponding hydrochloride salt (650 mg) by partitioning between 10% aqueous $NaHCO_3/CH_2Cl_2$ then evaporating to dryness) was dissolved in 10 mL of $CH_2Cl_2$ and added to the Pfp ester solution. The mixture was stirred at RT overnight then evaporated to dryness. The residue was taken up in 10 mL of EtOAc, cooled in ice and filtered to remove residual dicyclohexyl urea. The filtrate was diluted with hexane and cooled, yielding (32) as 640 mg white needles (53%), mp 127°–130° C. Anal. $C_{31}H_{42}N_2O_{10}$:C,H,N.

15-[[N-[N-[(1,1-dimethylethoxy)carbonyl]-L-Leucyl]-O-(phenylmethyl)-D-glutamyl]amino]-2,3,5,6,8,9,11,12-octahydro-1,4,7,10,13-benzopentaoxacyclopentadecin or 4'-[(Boc-L-Leu-OBzl-D-Glu)amino]benzo-15-crown-5 (33)

A solution of Boc-L-Leu-Pfp ester was prepared by reacting Boc-L-Leu (42 mg, 180 $\mu$mol), pentafluorophenol (33 mg, 180 $\mu$mol) and DCC (37 mg, 180 $\mu$mol) in 1.0 mL of $CH_2Cl_2$ (2 hr, RT). Dicyclohexylurea was removed by filtration. Crown ether (32) (100 mg, 170 $\mu$mol) was stirred in 25% $TFA/CH_2Cl_2$ (4 mL, 30 min, RT), then taken to dryness to rotary evaporation. The residue was taken up in $CH_2Cl_2$ (2 mL) then treated with excess triethylamine (660 mg, 6.6 mmol) and combined with the Boc-L-Leu-Pfp ester solution. After stirring at RT for 3 hr, the mixture was taken to dryness by rotary evaporation, giving a colorless oil which was purified first by silica gel chromatography (200 g of silica in a 5 cm dia. column eluted first with $CH_2Cl_2$, then with $CH_2Cl_2$:methanol (9:1)), then by preparative HPLC ($H_2O$:acetonitrile gradient) to yield product (33) as a white solid (70 mg. 67%), mp 123°–125° C. (shrinks at 60° C.). Anal. $C_{37}H_{52}H_3O_{11}$·½$H_2O$:C,H,N.

15-[[N-[N-[D-3-Hydroxydecanoyl]-L-Leucyl]-O-(phenylmethyl)-D-glutamyl]amino]-2,3,5,6,8,9,11,12-octahydro-1,4,7,10,13-benzopentaoxacyclopentadecin or 4'-[(D-3-hydroxydecanoyl-L-Leu-OBzl-D-Glu)amino]benzo-15-crown-5 (10)

Crown ether (33) (450 mg, 630 $\mu$mol) was stirred in 25% $TFA/CH_2Cl_2$ (10 mL, 30 min, RT) then taken to dryness by rotary evaporation. The residue was then stirred in $CH_2Cl_2$ (10 mL, 3 hr, RT) with pentafluorophenyl D-3-hydroxydecanoate (24) (220 mg, 630 $\mu$mol) and triethylamine (656 mg, 6.53 mmol). The reaction mixture was taken to dryness by rotary evaporation and purified by silica gel chromatography (200 g silica gel in a 5 cm dia. column eluted first with $CH_2Cl_2$, then with $CH_2Cl_2$:methanol (97.5:2.5)) followed by preparative HPLC ($H_2O$-acetonitrile gradient) to yield product 10 as a white solid (235 mg, 47%). A second purification by preparative HPLC was performed to obtain analytically pure material (45 mg, 9% overall yield), mp 120° C. (shrinks at 105° C.). CIMS ($NH_3$) m/z:786 (M+1); 803 (M+$NH_4$). Anal. $C_{42}H_{63}N_3O_{11}$·2$H_2O$:C,H,N.

15-[[N-[N-[D-3-Hydroxydecanoyl]-L-Leucyl]-D-glutamyl]amino]-2,3,5,6,8,9,11,12-octahydro-1,4,7,10,13-benzopentaoxacyclopentadecin or 4'-[(D-3-hydroxydecanoyl-L-Leu-D-Glu)amino]-benzo-15-crown-5 (11)

A mixture of crown ether 10 (197 mg, 250 $\mu$mol), ammonium formate (158 mg, 2.5 mmol) and 10% Pd·C (197 mg) was stirred in methanol (50 mL, 1.5 hr, RT) then filtered and evaporated to dryness. Purification by preparative HPLC (0.1% aq. TFA and a gradient of acetonitrile) yielded product (11) as a white solid (64 mg, 36%), mp 164°–167° C. CIMS ($NH_3$) m/z:695 (M+1); 713 (M+$NH_4$). Anal. $C_{35}H_{57}N_3O_{11}$·$H_2O$:C,H,N.

15-[[N-[N-[Decanoyl]-L-Leucyl]-O-(phenylmethyl)-D-glutamyl]amino]-2,3,5,6,8,9,11,12-octahydro-1,4,7,10,13-benzopentaoxacyclopentadecin or 4'-[(Decanoyl-L-Leu-OBzl-D-Glu)amino]benzo-15-crown-5 (12)

Crown ether (33) (450 mg, 630 μmol) was stirred in 25% TFA/CH$_2$Cl$_2$ (10 mL, 30 min, RT) then taken to dryness by rotary evaporation. The residue was dissolved idn CH$_2$Cl$_2$ (5 mL) and triethylamine added (656 mg, 6.53 mmol). Decanoic acid (210 mg, 630 μmol), pentafluorophenol (120 mg, 630 μmol) and DCC (130 mg, 630 μmol) were stirred in CH$_2$Cl$_2$ (20 mL, 3 hr, RT) then cooled in ice and dicyclohexyl urea removed by filtration. The filtrate was combined with the solution of deblocked (12) and stirred (3 hr, RT) then evaporated to dryness and purified by preparative HPLC (H$_2$O-acetonitrile gradient) to yield product (12) as a white solid (80 mg, 16%), mp 150° C. (shrinks at 120° C.). CIMS (NH$_3$) m/z:770 (M+1); 787 (M+HN$_4$). Anal. C$_{42}$H$_{63}$N$_3$O$_{10}$·H$_2$O:C,H,N.

15-[[N-[N-[Decanoyl]-L-Leucyl]-D-glutamyl]amino]-2,3,5,6,8,9,11,12-octahydro-1,4,7,10,13-benzopentaoxacyclopentadecinor4'-[(Decanoyl-L-Leu-D-Glu)amino]benzo-15-crown-5 (13)

A mixture of crown ether (12) (240 mg, 310 μmol), ammonium formate (197 mg, 3.1 mmol) and 10% Pd·C (240 mg) was stirred in methanol (50 mL, 4 hr, RT) then filtered and evaporated to dryness. Purification by preparative HPLC (H$_2$O:acetonitrile gradient) yielded product (13) as a white solid (30 mg, 14%). CIMS (NH$_3$) m/z:679 (M+); 697 (M+NH$_4$). Anal. C$_{35}$H$_{57}$N$_3$O$_{10}$·1½ H$_2$O:C,H,N.

di-(Dimethylethyl)-n-tetradecylmalonate (34)

A suspension of di-tert butyl malonate (10.80 g, 50 mmol) and t-BuOK (5.60 g, 50 mmol) was stirred (30 min, 75° C.) in t-BuOH (150 mL, dried over 4A sieves). To this was added a solution of 1-bromotetradecane (13.85 g, 50 mmol) and the reaction stirred at 75° C. overnight. Solvent was removed by rotary evaporation, giving a white semi-solid, which was partitioned between CH$_2$Cl$_2$ (100 mL) and saturated aqueous NaCl (2×300 mL), dried (MgSO$_4$) and evaporated to a colorless oil (15.3 g). Purification by silica gel flash chromatography (100% hexane incremented to hexane:CH$_2$Cl$_2$ (70:30)) gave product (34) as a colorless oil (10.0 g, 48%). High resolution FAB MS:C$_{25}$H$_{49}$O$_4$ (M+H); Theor. 413.3630855. Found 413.3627625.

A sample of (34) was treated with 100% TFA (10 min) then crystallized in hexane, yielding known n-tetradecylmalonate, mp 118°–121° C. (lit. mp 118°–120° C.; 123°–124° C.).

Benzyl-4,4-Dicarboxyoctadecanoate (36)

To a solution of di-(dimethylethyl)-n-tetradecylmaloanate (34) (4.12 g, (10.0 mmol) and t-BuOK (244 mg, 2.0 mmol) in t-BuOH (10mL, dried over 4A sieves) was added a solution of benzyl acrylate (1.62 g, 10.0 mmol in 5 mL t-BuOH). The initially colorless solution immediately turned brown. It was stirred (3 hr, RT) then additional t-BuOK (112 mg, 1.0 mmol) was added and the reaction continued overnight to yield (35). The mixture was neutralized with AcOH then evaporated to dryness and treated with neat TFA (20 mL, 1 hr) to removed the t-butyl groups. The TFA was removed by rotary evaporation, the residue dissolved in warm hexane, treated with activated charcoal then filtered. The filtrate provided fine white crystals which proved to be pasty when filtered. Drying provided product (36) as a white solid (2.31 g, 50%), mp 47°–49° C. High resolution FAB MS:C$_{27}$H$_{43}$O$_6$(M+H); Theor. 463.307147. Found 463:3059646. Anal. C$_{27}$H$_{42}$O$_6$·½ H$_2$O:C,H.

Benzyl-4-Carboxyoctadecanoate (8)

A solution of benzyl-4,4-dicarboxyoctadecanoate (36) (1.14 g, 2.5 mmol) in moist DMF (100 mL DMF; 1 mL H$_2$O) was stirred for 2 days (100°–105° C.) then solvent was removed by rotary evaporation. Crystallization from hexane yielded product (8) as a white solid (950 mg, 91%), mp 62°–63° C. High resolution FAB MS: C$_{26}$H$_{43}$O$_4$(M+H); Theor. 419.3161353. Found 419.3144060. Anal. C$_{26}$H$_{42}$O$_4$:C,H.

15-[2-[Benzyl-3-propanoyl]hexadecanoyl]amino]-2,3,5,6,8,9,11,12-octahydro-1,4,7,10,13-benzopentaoxacyclopentadecin (14)

A solution of benzyl-4-carboxyoctadecanoate (8) (318 mg, 760 μmol), pentafluorophenol (110 mg, 600 μmol) and DCC (160 mg, 780 μmol) was stirred in 4 mL of CH$_2$Cl$_2$ (½ hr, RT). Dicyclohexylurea side product was removed by filtration. A total of 500 μmol of aminobenzo-15-crown-5 (31) (obtained from the corresponding hydrochloride salt (160 mg) by partitioning between 10% aqueous NaHCO$_3$/CH$_2$Cl$_2$ then evaporating to dryness) was dissolved in 4 mL of CH$_2$Cl$_2$ and added to the Pfp ester solution. The mixture was stirred at RT overnight then evaporated to dryness. Purification by preparative HPLC (0.1% TFA in a H$_2$O-acetonitrile gradient system) yielded product (14) as a white solid (350 mg, 100%). FAB MS m/z:684 (M+1); 632 (M-Bzl+K$^+$); 594 (M+1-Bzl).

15-[2-[3-propanoyl]hexadecanoyl]amino]-2,3,5,6,8,9,11,12-octahydro-1,4,7,10,13-benzopentaoxacyclopentadecin (15)

A mixture of crown ester (14) (137 mg, 200 μmol), ammonium formate (126 mg, 2.0 mmol) and 10% Pd·C (50 mg) was stirred in methanol (10 mL, 2 hr, RT) then filtered, evaporated to dryness and partitioned between dilute aqueous HCl (30 mL) and CHCl$_3$ (2×30 mL). The organic phase was dried (MgSO$_4$), evaporated to dryness and lyophilized from dioxane yielding (15) as a white solid (84 mg, 71%), mp 70°–75° C. (shrinks at 40° C.). CIMS (NH$_3$) m/z:594 (M+1); 611 (M+NH$_4$). FAB MS m/z: 594 (M+1); 616 (M+Na$^+$) Anal. C$_{33}$H$_{55}$NO$_8$·2H$_2$O:C,H,N.

EXAMPLE 4

Biological Assays of Viscosin Analogs

Lysis of L. Donovani

For the purpose of determining the ability of viscosin analogs to lyse the parasite *Leishmania donovani*, the parasites were harvested from culture medium M199+5% fetal bovine serum (FBS), washed twice in Hanks Balanced Salts Solution (HBSS) and resukspended in same at 1×10$^8$ per mL. The requisite amount of compound at a concentration of 10 mg/mL in water (compounds (1), (9), and (10)) or in ethanol was added and the cultures examined at 4 hr and after overnight at 27° C.

For the purpose of determining the effect of the compounds on the growth of parasite in serum-containing and serum-free medium, the parasites were harvested from culture medium M199+5% FBS, washed twice in HBSS and resuspended in same at 1×10$^8$/mL. Serum-containing M199 ans serum-free REIII media were filtered and sterilized prior to use. The washed cells were added to achieve an initial concentration of 1.66×10$^6$ cells/mL. Cell densities were determined by hemacytometry at 21 hr, and in some cases at 43 hr of incubation at 27° C.

TABLE I

Lowest concentration with activity against L. Donovani

| Compound[1] | Lysis mg/ml | Growth mg/ml | Growth (Serum Free Medium) mg/ml |
|---|---|---|---|
| 1 | 100 | 100 | 100 |
| 4 | | (not tested)[2] | |
| 5 | | (no effect) | |
| 6 | | (no effect) | |
| 7 | | (no effect) | |
| 14 | 30 | 100 | $10^3$ |
| 15 | 30 | 30 | $10^3$ |
| 10 | 30 | 100 | $100^3$ |
| 11 | | (no effect) | |
| 12 | 100 | (no effect[4]) | |
| 13 | | (no effect) | |

[1]As numbered in the Examples.
[2]Insoluble in water.
[3]Lowest effective concentration determined.
[4]May have come out of solution and filtered out.

Inhibition of HSV-2 Growth

For the purpose of determining the ability of viscosin analogs to inhibit Herpes Simplex Virus 2 (HSV-2), viral particles are used to infect any of the many cultured cell types which support HSV-2 growth. (Davis, B., Chapter 55 in *Microbiology, Including Immunology and Molecular Genetics,* 3rd Ed., Harper & Row, Philadelphia (1980), p. 1064). Particularly preferred host cells are rabbit skin cells or Vero cells. (Grammer, S., et al., *J. Immunol.* 145:2249–2253 (1990); Gao, W., et al., *J. Biol. Chem.* 265:20172–20178 (1990)). The lowest concentration at which 50% of the viruses are rendered noninfective during culture with cells treated with a viscosin analog is determined by known methods. (See, e.g., Groupe, V., et al., *Proc. Soc. Exptl. Biol. Med.* 78:354–358 (1951); Mitsuya, H., et al., *Science* 226:172–174 (1984)). Acyclovir, a known anti-herpesviral agent (Douglas, R., Chapter 51 in *Goodman and Gilman's the Pharmacological Basis of Therapeutics,* 8th Ed., G. Gilman et al., eds., Pergamon Press, New York (1980)), was used as a positive control.

TABLE II

Activity of Viscosin analogs against HSV-2

| Compound | Structure[1] | HSV-2 $LD_{50}$ (μg/ml) | Cell Toxicity (μg/ml) |
|---|---|---|---|
| Viscosin | 1 | 7–18 | 50–100 |
| Deshydroxy Viscosin | 3 | 19–28 | 100 |
| Deshydroxy L-Leu-D-Glu Octadecanoyl Viscosin | 4 | >100 | >100 |
| Viscosic Acid | 5 | >100 | >100 |
| D-3-Hydroxydecanoyl-L-Leu-D-Gluamide | 7 | >100 | >100 |
| D-3-Hydroxydecanoyl-L-Leu-OBzl-D-Glu-benzo-15-Crown-5-ether | 10 | >100 | >100 |
| D-3-Hydroxydecanoyl-L-Leu-D-Glu benzo-15-Crown-5-ether | 11 | >100 | >100 |
| Decanoyl-L-Leu-OBzl-D-Glu benzo-15-Crown-5-ether | 12 | >50 | 100 |
| Decanoyl-L-Leu-D-Glu benzo-15-Crown-5-ether | 13 | >100 | >100 |
| Bzl-γ-carboxyl octadecanoyl benzo-15-Crown-5-ether | 14 | >33 | 100 |
| γ-carboxy octadecanoyl benzo-15-Crown-5-ether | 15 | 11 | 33 |
| Acetyl benzo-15-Crown-5-ether | 16 | >100 | >100 |
| Octadecanoyl benzo-15-Crown-5-ether | 42 | >100 | >100 |
| Acyclovir | — | 0.6–1.5 | |

[1]As numbered in the Examples.

Antimycobacterial Activity

In order to determine the ability of viscosin analogs to act as antimycobacterial agents, a variety of known methods for determining antibiotic sensitivity may be used. (See, generally, Wistreich, G., *Microbiology,* 3rd Ed., Codllier, London (1980), pp. 399–403). Specific strains of M. tb. or M. bovis to be tested are obtained from individual patients suffering from TB or from the American Type Culture Collection (*ATCC Catalogue of Bacteria and Phages,* 18th Ed., Gherna et al., eds., ATCC, Rockville, Md. (1992), pp. 201–212). Culture media and methods for measuring growth for M. tb. and M. bovis are as previously described (*Manual of Methods for General Bacteriology,* Gerhardt et al., eds., American Socy. for Microbiol., Washington, D.C. (1981)).

In the susceptibility test, equal amounts of isolated cultures of M. tb. or M. bovis are used to inoculate media supplemented with serial dilutions of the analog to be tested. If necessary, the pH of a concentrated aqueous solution of a viscosin analog is adjusted to ensure solubility of the analog. In the latter instance, solutions having the same pH as the solution of viscosin analog are used as controls for pH effects upon bacterial growth. In this assay, Minimum Inhibitory Concentrations (MICs) are defined as the lowest concentrations of analog at which to visible growth is observed. (Haneishi, T., et al., *Antimicrob. Agents Chemother.* 32:110–116 (1988)). A simpler version of the susceptibility test can be performed with solid agar media in which a concentration gradient of a viscosin analog has been established. (Gherna, R., Chapter 12 in *Manuals of Methods for General Bacteriology,* P. Gerhardt et al., eds., American Society for Microbiology, Washington, D.C. (1981), p. 230).

Because various subpopulations of M. tb. are usually present in different tissues in a TB patient, combinations of antibiotics are often used in treating TB. (U.S. Congress, Office of Technology Assessment, *The Continuing Challenge of Tuberculosis,* OTA-H-574, U.S. Government Printing Office, Washington, D.C. (1993), p. 74). Thus, it is important to evaluate viscosin analogs for synergistic effects with each other and with other antimycobacterial agents. The synergism of pairs of compounds is tested via the checkerboard method. (Haneishi, T., et al., *Antimicrob. Agents Chemother.* 32:110–116 (1988)). Briefly, freshly cultured cells of a mycobacterial species that is to be tested are suspended in fresh media containing a viscosin analog and one or more other antimycobacterial agents in serial twofold dilutions ranging from 0 to 1 mg/mL. For each combination of antimycobacterial agents, MICs are determined after 1 or 2 weeks of incubation at 37° C. The Fractional Inhibitory Concentrations (FICs) for each component are calculated based on the following formula: FIC=(MIC of antimycobacterial agent in combination/MIC of antimycobacterial agent alone) +(MIC of viscosin analog in combination/MIC of viscosin analog alone). A minimal FIC of the respective FICs is defined as an FIC index. A synergistic effect is one with an FIC index <0.5; an antagonistic effect is reflected by an FIC index >4.

Several nonhuman animals support the pathogenic growth of mycobacterial species with symptoms resembling those seen in humans and are thus accepted in the art as correlating with humans for the purpose of determining the tissue distribution, pharmacokinetics and in vivo efficacy of antimycobacterial agents. These animal models include, but are not limited to, mice, rats, dogs, pigs, cows, horses, rabbits, nonhuman primates and guinea pigs. (Haneishi, T., et al., *Antimicrob. Agents Chemother.* 32:110–116 (1988); *The Merck Veterinary Manual,* 6th Ed., Fraser et al., eds., Merck & Co., Rahway, N.J. (1986), pp. 401–406; Wolinsky, E., Chapter 37 in *Microbiology Including Immunology and Molecular Genetics,* 3rd Ed., Davis et al., eds., Harper & Row, Philadelphia (1980), p. 724; *Hagan and Bruner's Microbiology and Infectious Diseases of Domestic Animals,* 8th Ed., Timoney et al., eds., Comstock Publishing Associates, Ithaca (1988), pp. 270–289).

Presently, TB resulting from multidrug-resistant strains of M. tb. (MDR-TB) presents significant challenges to the treating physician. (Bloom, B., et al., *Science* 257:1055–1064 (1992); U.S. Congress, Office of Technology Assessment, *The Continuing Challenge of Tuberculosis,* OTA-H-574, U.S. Government Printing Office, Washington, D.C. (1993), pp. 69–80). Because viscosin is an antimycobacterial agent that is more effective against antibiotic resistant strains of M. tb. (Kochi, M., et al., *Bact. Proc.* 29–30 (1951)), the viscosin analogs of the invention are especially useful in treating MDR-TB, alone or in combination with other drugs previously used to treat non-multidrug-resistant TB (Daniel, T.M., Chapter 119 in *Harrison's Principles of Internal Medicine,* 11th Ed., Braunwald et al., eds., McGraw-Hill Co., New York (1987), pp. 625–633; Mandell, G. L., et al., Chapter 49 in *Goodman and Gilman's the Pharmacological Basis of Therapeutics,* 8th Ed., Gilman et al., eds., Pergamon Press, New York (1990), pp. 1146–1164).

Treatment of individuals suffering from TB with the visocosin analogs of the invention can be customized to match the antibiotic sensitivity of the particular M. tb. strain(s) with lwhich an individual is infected. That is, cultures of M. tb. isolated from a TB patient are tested for their susceptibility to various viscosin analogs, alone or in combination with each other or other drugs, in order to select the most effective antibiotic regiment for an individual patient. In order to begin treatment as quickly as possible, methods for rapidly assessing the susceptibility of M. tb. strains to antibiotics may be employed. (Jacobs, W., et al., *Science* 260:819–822 (1993)).

Biosurfactant Activity

For the purpose of determining the ability of viscosin analogs to act as surfactants, the critical micelle concentration (CMC) of each analog is measured. The CMC of a compound is, in effect, the solubility of a surfactant within an aqueous phase. At concentrations exceeding the CMC, suppramolecular structures such as bilayers, vesicles and micelles readily form. (Georgiou, G., et al., *Bio/Technology* 10:60–65 (1992)).

Viscosin has been found to be a potent biosurfactant (Laycock, M., et al., *J. Agric. Food Chem.* 39:483–489 (1991)). The viscosin analogs of the invention comprise biosurfactants with properties that differ from those of native viscosin dues to the presence of substituted, modified or additional chemical groups in the analogs. Analogs with surfactant activity are initially identified by using emulsifying test as a screening procedure. (Neu, T., et al., *Appl. microbiol. Biotechnol.* 32:521–525 (1990)). The methods used to determine the CMC of viscosin (~0.1 mg/ml; Neu, T., et al., *Appl. Microbiol. Biotechnol.* 32:518–520 (1990)) are used to evaluate the CMC of viscosin analogs that demonstrate activity in the emulsifying test.

Utility of the Invention

The embodiments of the invention described herein can be used for the following purposes, alone or in combination with each other or other complementary methods and/or compositions.

The viscosin analogs of the invention may be used as antiviral, antitrypanosomal and/or antibacterial agents. Aspects of this utility is the use of the viscosin analogs of the invention for the treatment of Chagas' disease and TB, particularly MDR-TB.

The viscosin analogs of the invention may also be used as biosurfactants for the emulsification of compounds when it is desired to use biodegradable surfactants and/or surfactants which are chemically compatible with particular molecules of interest.

Incorporation by Reference

The entire text of all publications cited herein are hereby incorporated by reference. It is understood that these descriptions, examples and embodiments are for illustrative purposes only, and that various modifications would be suggested within the spirit and purview of this application and the scope of the appended claims.

What is claimed is:

1. A linear viscosin analog selected from the group consisting of: D-3-Hydroxydecanoyl-L-Leu-D-Glu-$NH_2$; or

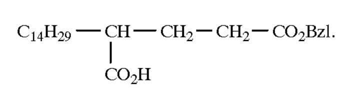

.

2. A viscosin analog having the following formula:

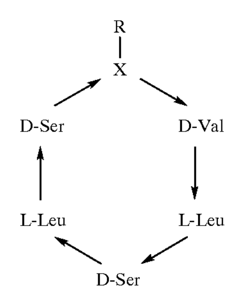

wherein X is D- or L-Lys or Orn, and wherein R is D-3-hydroxydecanoyl-L-Leu-D-Glu, Decanoyl-L-Leu-D-Glu, Octadecanoyl, linear $C_2$ to $C_{22}$ amides, or D-3-hydroxydecanoyl-L-$X_1$-$X_2$, wherein $X_1$ is Ile, Val, Gly, or Norisoleucine and wherein $X_2$ is D-Asp, D-γGlu, D-βAsp, Succinic acid, or dicarboxylic acid.

3. A viscosin analog having the following formula:

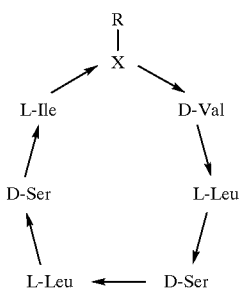

wherein X is Dbu, and wherein R is D-3-hydroxydecanoyl-L-Leu-D-Glu, Decanoyl-L-Leu-D-Glu, Octadecanoyl, linear $C_2$ to $C_{22}$ amides, or D-3-hydroxydecanoyl-L-$X_1$-$X_2$, wherein $X_1$ is Ile, Val, Gly, or Norisoleucine and wherein $X_2$ is D-Asp, D-γGlu, D-βAsp, Succinic acid, or dicarboxylic acid.

4. A viscosin analog having the following formula:

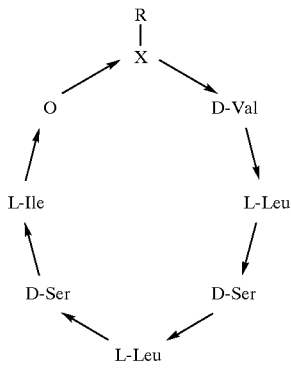

wherein X is D-allo-Thr, D-Thr, D-Ser, or Homoserine and wherein R is D-3-hydroxydecanoyl-L-Leu-D-Glu, Decanoyl-L-Leu-D-Glu, Octadecanoyl, linear $C_2$ to $C_{22}$ amides, or D-3-hydroxydecanoyl-L-$X_1$-$X_2$, wherein $X_1$ is Ile, Val, Gly, or Norisoleucine and wherein $X_2$ is D-Asp, D-γGlu, D-βAsp, Succinic acid, or dicarboxylic acid, provided that X is not D-allo-Thr when R is D-3-hydroxydecanoyl-L-Leu-D-Glu.

5. A compound having the following formula:

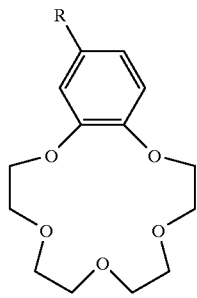

wherein R is
  $C_2$–$C_{22}$ aliphatic amides;
  $C_2$–$C_{22}$ fatty acyl amides;
  D-3-hydroxydecanoyl-L-$X_1$-D-$X_2$-NH; or
  Decanoyl-L-$X_1$-D-$X_2$-NH, $X_1$ is a neutral amino acid and wherein $X_2$ is an acidic or a neutral amino acid.

6. The compound of claim 5, wherein R is Acetyl NH.

7. The compound of claim 5, wherein R is a D-3-hydroxydecanoyl-L-$X_1$-D-$X_2$-NH, wherein $X_1$ is a neutral amino acid and wherein $X_2$ is an acidic or a neutral amino acid, selected from the group consisting of D-3-Hydroxydecanoyl-L-Leu-OBzl-D-Glu-NH; and D-3-Hydroxydecanoyl-L-Leu-D-Glu-NH.

8. The compound of claim 5, wherein R is a Decanoyl-L-$X_1$-D-$X_2$-NH, wherein $X_1$ is a neutral amino acid and wherein $X_2$ is an acidic or a neutral amino acid, selected from the group consisting of Decanoyl-L-Leu-OBzl-D-Glu-NH and Decanoyl-L-Leu-D-Glu-NH.

9. The compound of claim 5, wherein R is a $C_2$–$C_{22}$ fatty acyl amide selected from the group consisting of

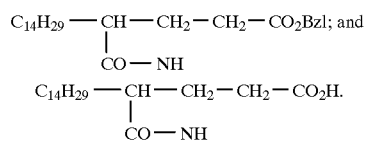

10. A pharmaceutical composition comprising the viscosin analog of any one of claims 1–4 and a pharmaceutically acceptable carrier.

11. A method of inhibiting the growth of Herpesvirus, comprising contacting cells infected with one or more Herpesvirus with the viscosin analog of any one of claims 1–4.

12. A method of inhibiting the growth of a Mycobacterium, comprising contacting said Mycobacterium with the viscosin analog of any one of claims 1–4.

13. A method of inhibiting the growth of a trypanosome, comprising contacting cells infected with one or more trypanosomes with the viscosin analog of any one of claims 1–4.

14. A pharmaceutical composition comprising a compound of claim 5 and a pharmaceutically acceptable carrier.

15. A method of inhibiting the growth of Herpesvirus, comprising contacting cells infected with one or more Herpesvirus with a compound of claim 5.

16. A method of inhibiting the growth of a Mycobacterium, comprising contacting said Mycobacterium with a compound of claim 5.

17. A method of inhibiting the growth of a trypanosome, comprising contacting cells infected with one or more trypanosomes with a compound of claim 5.

18. The method of claim 11, wherein said Herpesvirus is Herpes Simplex Virus 2.

19. The method of claim 12, wherein said Mycobacterium is selected from the group consisting of *M. tuberculosis, M. intracellulare, M. bovis, M. gordonae, M. kansasii*, and *M. nonchromogenicum*.

20. The method of claim 13, wherein said trypanosome is *Trypanosoma cruzi*.

21. The method of claim 12, wherein said Mycobacterium is *M. tuberculosis*.

22. The method of claim 12, wherein said Mycobacterium is resistant to one or more antibiotics selected from the group consisting of cycloserine, streptomycin, neomycin, penicillin, ampicillin, amoxicillin, rifampicin, tetracycline, kanamycin, amikacin, capreomycin, isoniazid, p-aminosalicyclic acid, ethambutol, rifampin, pyrazinamide, thioacetazone, viomycin, ethionamide, ofloxacin and dihydromycoplanecin A.

23. The method of claim 16, whreein said Mycobacterium is resistant to one or more antibiotics selected from the group consisting of cycloserine, streptomycin, neomycin, penicillin, ampicillin, amoxicillin, rifampicin, tetracycline, kanamycin, amikacin, capreomycin, isoniazid, p-aminosalicyclic acid, ethambutol, rifampin, pyrazinamide, thioacetazone, viomycin, ethionamide, ofloxacin and dihydromycoplanecin A.

24. A composition which acts as a surfactant, comprising at least one of the viscosin analogs of any one of claims 1–4 and 5–9.

* * * * *